US006866844B2

(12) United States Patent
Qin et al.

(10) Patent No.: US 6,866,844 B2
(45) Date of Patent: Mar. 15, 2005

(54) PRECURSOR N-ACETYLGALACTOSAMINE-4-SULFATASE, METHODS OF TREATMENT USING SAID ENZYME AND METHODS FOR PRODUCING AND PURIFYING SAID ENZYME

(75) Inventors: Minmin Qin, Pleasanton, CA (US); John M. Henstrand, Davis, CA (US); Gary N. Zecherle, Novato, CA (US); Dan J. Wendt, Walnut Creek, CA (US); Wai-Pan Chan, Castro Valley, CA (US); Lin Chen, San Francisco, CA (US); Paul A. Fitzpatrick, Albany, CA (US); Christopher M. Starr, Sonoma, CA (US)

(73) Assignee: Biomarin Pharmaceutical Inc., Novato, CA (US)

( * ) Notice: Subject to any disclaimer, the term of this patent is extended or adjusted under 35 U.S.C. 154(b) by 0 days.

(21) Appl. No.: 10/290,908

(22) Filed: Nov. 7, 2002

(65) Prior Publication Data

US 2004/0101524 A1 May 27, 2004

Related U.S. Application Data

(63) Continuation-in-part of application No. 10/704,365, filed on Nov. 7, 2003.

(51) Int. Cl.$^7$ .......................... A61K 38/46; C12N 9/16; C12N 1/20; C12N 15/00; A23J 1/00
(52) U.S. Cl. ................... 424/94.6; 435/196; 435/252.3; 435/320.1; 435/536; 435/23.2; 435/530; 435/412
(58) Field of Search .......................... 424/94.6; 435/196, 435/252.3, 320.1; 536/23.2; 530/412

(56) References Cited

FOREIGN PATENT DOCUMENTS

WO    WO 01/83722    11/2001

OTHER PUBLICATIONS

Anson, et al., "Correction of Human Mucopolysaccharidosis Type–VI Fibroblasts with Recombinant N–Acetylagalactosamine–4–Sulphatase," *Biochem. J.* 284:789–794 (1992).
Bielicki, et al., "Advantages of Using Same Species Enzyme for Replacement Therapy in a Feline Model of Mucopolysaccharidosis Type VI," *Journal of Biological Chemistry*, 274(51):36335–36343 (1999).
Brooks, et al., "Enzyme Replacement Therapy In Mucopolysaccharidosis VI: Evidence for Immune Response S and Alteed Efficacy of Treatment in Animal Models," *Biochim. Biophys. Acta*, 1361:203–216 (1997).
Byers, et al., "Effect of Enzyme Replacement Therapy on Bone Formation in a Feline Model of Mucopolysaccharidosis Type VI," *Bone*, 21(5):425–431 (1997).
Crawley, et al., "Enzyme Replacement Therapy from Birth in a Feline Model of Mucopolysaccharidosis Type VI," *J. Clin. Invest.*, 99(4):651–662 (1997).
Crawley, et al., "Enzyme Replacement Therapy from Birth in a Feline Model of Maroteaux–Lamy Syndrome," *J. Clin. Invest.*, 97(8):1864–1873 (1996).
Haskins, et al., "Spinal Cord Compression and Hindlimb Paresis in Cats with Mucopolysaccharidosis VI," *J. Am. Vet. Med. Assoc.*, 182:983–985 (1983).
Haskins, et al., "The Pathology of the Feline Model of Mucopolysaccharidosis VI.," *Am. J. Pathol.*, 101:657–674 (1980), Abstract.
Hoogerbrugge, et al., "Allogenic Bone Marrow Transplantation for Lysosomal Storage Diseases," *Lancet*, 345:1398–1402 (1995).
Inherited Disease, eds. Scriver t al., New York:McGraw–Hill, 1989, pp. 1565–1587.
Jezyk, et al., "Mucopolysaccharidosis in a Cat with Arysulfatase B Deficiency: A Model of Maroteaux–Lamy Syndrome," *Science* 198:834–836 (1977).
Konde, et al., "Radiographically Visualized Skeletal Changes Associated with Mucopolysaccharidosis Vl in Cats," *Vet Radiol.*, 28(6):223:228 (1987).
Krivit, et al. "Bone–Marrow Transplantation In The Maroteaux–Lamy Syndrome (Mucopolysaccharidosis Type Vi)," *N. Eng. J. Med.*, 311(25):1606–1611 (1984).
Krivit, "Maroteaux–Lamy Syndrome—Treatment b. Allogeneic Bone Marrow Transplantation in 6 Patients and Potential for Antotransplantation Bone Marrow Gene Insertion," *Intl. Ped.* 7:47–52 (1992).
McGovern, et al., "Purification and Properties of Feline and Human Arylsulfatase B Isozymes," *J. Biol. Chem.* 257:12605–12610 (1982).
Peters, et al. "Phylogenetic Conservation of Arylsulfatases," *J. Biol. Chem.*, 265(6)3374–3381 (1990).
Roberts, et al., "Development of a Procedure for Purification of a Recombinant Therapeutic Protein," *Australasien Biotechnol.*, 6(2):93–99 (1996).
Yogalingam, et al., "Regulation of N–acetylgatactosamine 4–Sulfatase Expression in Retrovirus–Transduced Feline Mucopolysaccharidosis Type VI Muscle Cells," *DNA Cell Biol.*, 18(3):187–195 (1999).

*Primary Examiner*—Tekchand Saidha
(74) *Attorney, Agent, or Firm*—Marshall, Gerstein & Borun LLP

(57) ABSTRACT

The present invention provides a highly purified recombinant human precursor N-acetylgalactosamine-4-sulfatase and biologically active mutants, fragments and analogs thereof as well as pharmaceutical formulations comprising highly purified recombinant human precursor N-acetylgalactosamine-4-sulfatase. The invention also provides methods for treating diseases caused all or in part by deficiencies in human N-acetylgalactosamine-4-sulfatase including MPS VI and methods for producing and purifying the recombinant precursor enzyme to a highly purified form.

47 Claims, 15 Drawing Sheets

Outline of the rhASB Drug Substance Purification Process

Process Flow Chart - Sampling Plan

SDS-PAGE, 4-20% TG gel
Silver Stain 4-20% Polyacrylamide gradient SDS gels, stained with Coomassie R-250 or Silver 1 NEB Broad Range Prestained Standards
2 5 µg ASB AS60001 (Batch Process)
3 5 µg Ap60109UF4
4 5 µg Ap60109UF10
5 5 µg Ap60109UF15

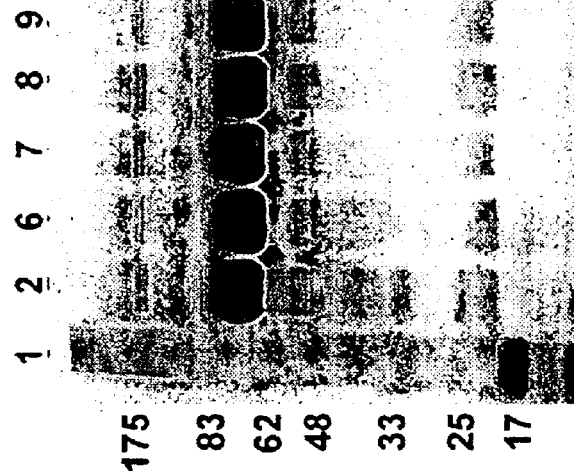
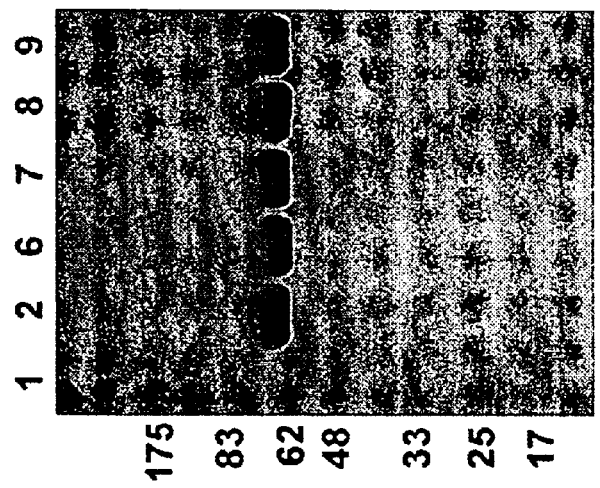
4-20% Polyacrylamide gradient SDS gels, stained with Coomassie R-250 or Silver
1 NEB Broad Range Prestained Standards
2 5 μg ASB AS60001 (Batch Process)
3 5 μg Ap60109UF4
4 5 μg Ap60109UF10
5 5 μg Ap60109UF15
6 5 μg Ap60109UF18
7 5 μg Ap60109UF22
8 5 μg Ap60109UF25
9 5 μg Ap60109UF27

Formulated rhASb, 052202
5 ug/lane

1. AP60202 UF 4
2. AP60202 UF 10
3. AP60202 UF 18
4. AP60202 (BMK)
5. 102PD0139xB3
6. 102PD0139xB5
7. rhASB-202-002
8. 102PD0136 P1
9. 102PD0136 P2
10. Mark 12 Standard

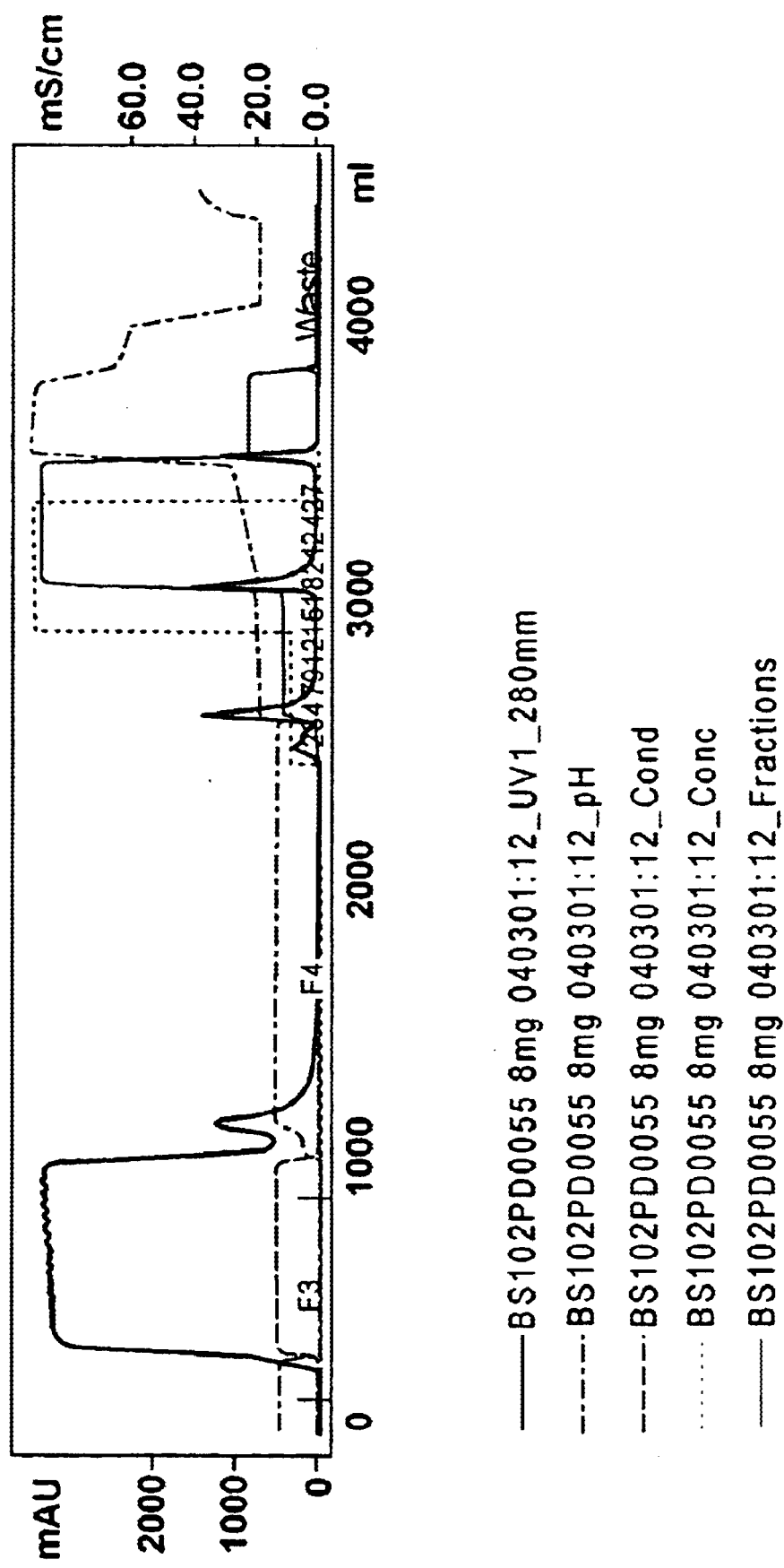

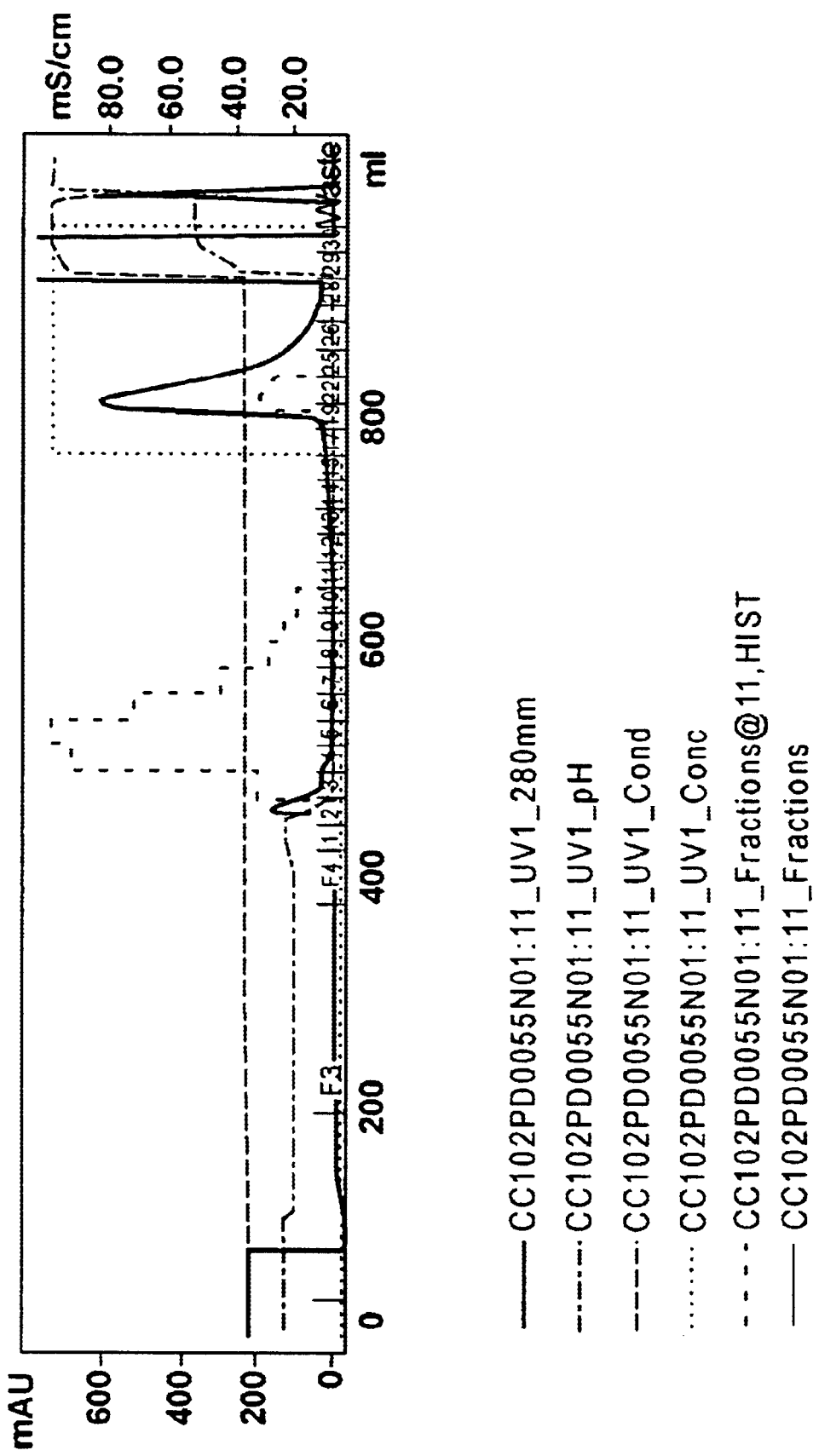

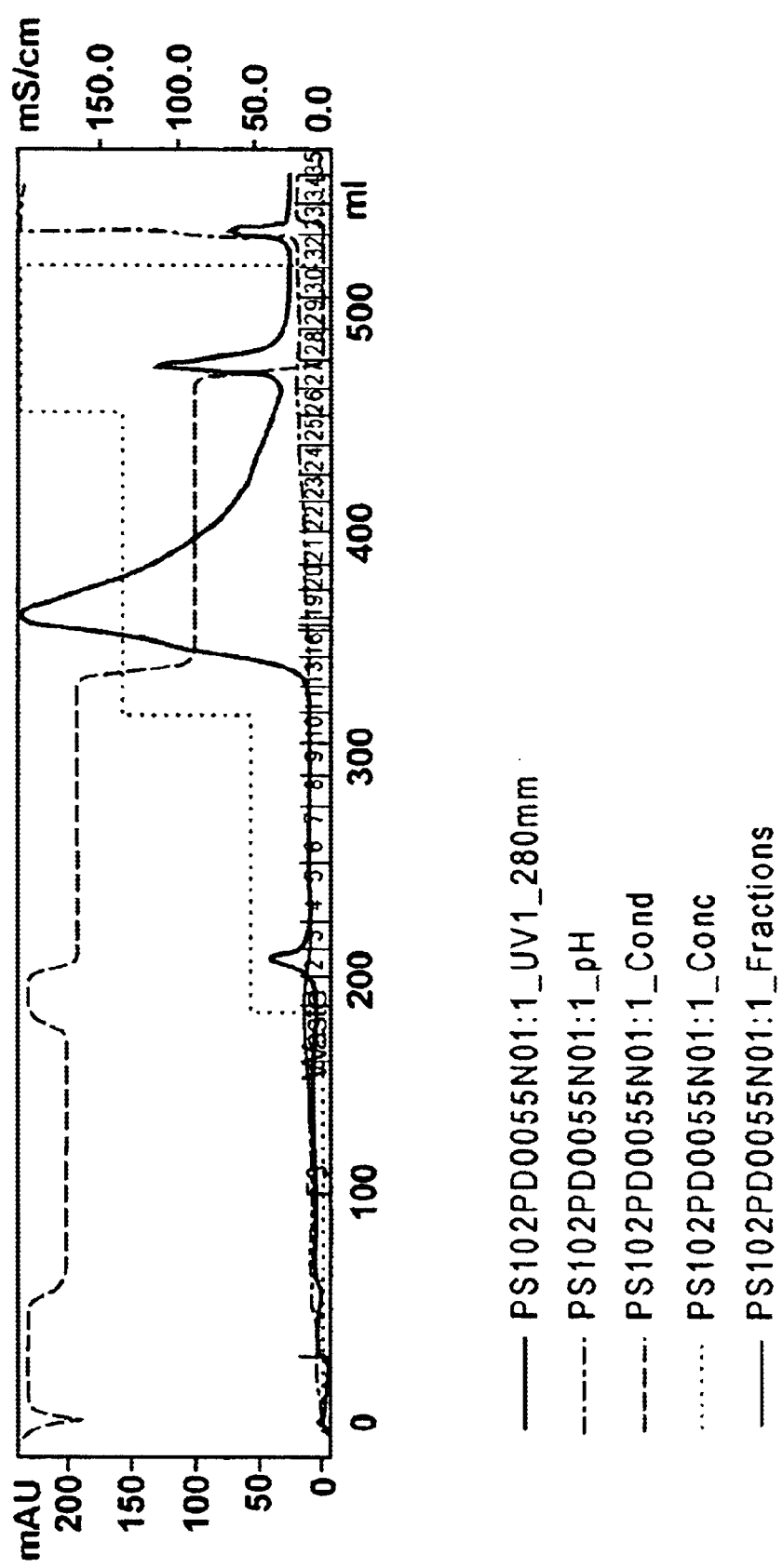

Western Blot, G-Anti-Cathepsin IgG, M19, 1:5,000
Donkey-Anti_goat IgG AP1:5,000

PRECURSOR N-ACETYLGALACTOSAMINE-4-SULFATASE, METHODS OF TREATMENT USING SAID ENZYME AND METHODS FOR PRODUCING AND PURIFYING SAID ENZYME

This application is a Continuation-in-part of U.S. Ser. No. 10/704,365, filed Nov. 7, 2003, now pending.

FIELD OF THE INVENTION

The present invention features therapeutics and methods for treating mucopolysaccharidosis VI as well as production and purification procedures for producing such therapeutics.

BACKGROUND OF THE INVENTION

MPS VI (Maroteaux-Lamy syndrome) is a lysosomal storage disease in which the affected patients lack the enzyme N-acetylgalactosamine-4-sulfatase (ASB). The enzyme metabolizes the sulfate moiety of glycosaminoglycan (GAG) dermatan sulfate (Neufeld, et al., "The mucopolysaccharidoses" The Metabolic Basis of Inherited Disease, eds. Scriver et al., New York: McGraw-Hill, 1989, p. 1565–1587). In the absence of the enzyme, the stepwise degradation of dermatan sulfate is blocked and the substrate accumulates intracellularly in the lysosome in a wide range of tissues. The accumulation causes a progressive disorder with multiple organ and tissue involvement in which the infant appears normal at birth, but usually dies before puberty. The diagnosis of MPS VI is usually made at 6–24 months of age when children show progressive deceleration of growth, enlarged liver and spleen, skeletal deformities, coarse facial features, upper airway obstruction, and joint deformities. Progressive clouding of the cornea, communicating hydrocephalus, or heart disease may develop in MPS VI children. Death usually results from respiratory infection or cardiac disease. Distinct from MPS I, MPS VI is not typically associated with progressive impairment of mental status, although physical limitations may impact learning and development. Although most MPS VI patients have the severe form of the disease that is usually fatal by the teenage years, affected patients with a less severe form of the disease have been described which may survive for decades.

Several publications provide estimates of MPS VI incidence. A 1990 British Columbia survey of all births between 1952 and 1986 published by Lowry et al (Lowry, et al., Human Genet 85:389–390 (1990)) estimates an incidence of just 1:1,300,000. An Australian survey (Meikle et al., JAMA 281(3):249–54) of births between 1980–1996 found 18 patients for an incidence of 1:248,000. A survey in Northern Ireland (Nelson, et al., Hum. Genet. 101:355–358 (1997)) estimated an incidence of 1:840,000. Finally, a survey from The Netherlands from 1970–1996 calculated a birth prevalence of 0.24 per 100,000 (Poorthuis, et al., Hum. Genet. 105:151–156 (1999)). Based on these surveys, it is estimated that there are between 50 and 300 patients in the U.S. who are diagnosed with all forms of this syndrome.

There is no satisfactory treatment for MPS VI although a few patients have benefited from bone marrow transplantation (BMT) (Krivit, et al., N. Engl. J. Med. 311(25):1606–11 (1984); Krivit, et al., Int. Pediat. 7:47–52 (1992)). BMT is not universally available for lack of a suitable donor and is associated with substantial morbidity and mortality. The European Group for Bone Marrow Transplantation reported transplant-related mortality of 10% (HLA identical) to 20–25% (HLA mismatched) for 63 transplantation cases of lysosomal disorders (Hoogerbrugge, et al, Lancet 345: 1398–1402 (1995)). Other than BMT, most patients receive symptomatic treatment for specific problems as their only form of care. It is an object of the present invention to provide enzyme replacement therapy with recombinant human N-acetylgalactosamine-4-sulfatase (rhASB). No attempts to treat humans with rhASB have been made. Likewise, no acceptable clinical dosages or medical formulations have been provided. Several enzyme replacement trials in the feline MPS VI model have been conducted.

SUMMARY OF THE INVENTION

The present invention encompasses the production, purification, and the use of a composition comprising a highly purified N-acetylgalactosamine-4-sulfatase in the precursor form.

In a first aspect, the present invention features novel methods of treating diseases caused all or in part by a deficiency in N-acetylgalactosamine-4-sulfatase (ASB). A method comprises administering an effective amount of a pharmaceutical composition to a subject in need of such treatment. In the preferred embodiment, the pharmaceutical composition comprises highly purified N-acetylgalactosamine-4-sulfatase in the precursor form, or a biologically active fragment, mutant or analog thereof alone or in combination with a pharmaceutically suitable carrier. The subject suffers from a disease caused all or in part by a deficiency of N-acetylgalactosamine-4-sulfatase. In other embodiments, this method features transferring a nucleic acid encoding all or a part of an N-acetylgalactosamine-4-sulfatase (ASB) or a biologically active mutant or analog thereof into one or more host cells in vivo. Preferred embodiments include optimizing the dosage to the needs of the organism to be treated, preferably mammals or humans, to effectively ameliorate the disease symptoms. In preferred embodiments the disease is mucopolysaccharidosis VI (MPS V1) or Maroteaux-Lamy syndrome.

In a second aspect, the present invention features novel pharmaceutical compositions comprising an N-acetylgalactosamine-4-sulfatase (ASB) or a biologically active fragment, mutant or analog thereof useful for treating a disease caused all or in part by a deficiency in N-acetylgalactosamine-4-sulfatase (ASB). In the preferred embodiment, the N-acetylgalactosamine-4-sulfatase is precursor N-acetylgalactosamine-4-sulfatase. Such compositions may be suitable for administration in a number of ways such as parenteral, topical, intranasal, inhalation or oral administration. Within the scope of this aspect are embodiments featuring nucleic acid sequences encoding all or a part of an N-acetylgalactosamine-4-sulfatase (ASB) which may be administered in vivo into cells affected with an N-acetylgalactosamine-4-sulfatase (ASB) deficiency.

In a third aspect, the present invention features a method to produce an N-acetylgalactosamine-4-sulfatase (ASB) or a biologically active fragment, mutant or analog thereof in amounts which enable using the enzyme therapeutically. In a broad embodiment, the method comprises the step of transfecting a cDNA encoding for all or a part of a N-acetylgalactosamine-4-sulfatase (ASB) or a biologically active mutant or analog thereof into a cell suitable for the expression thereof. In the preferred embodiment, the cells are grown in a constant or continuous culture or in perfusion. In another preferred embodiment, the cells are grown in a medium that lacks G418. In some embodiments, a cDNA encoding for a complete N-acetylgalactosamine-4-sulfatase (ASB) is used, preferably a human N-acetylgalactosamine- 4-sulfatase (ASB). However, in other embodiments, a cDNA encoding for a biologically active fragment or mutant thereof may be used. Specifically, one or more amino acid substitutions may be made while preserving or enhancing the biological activity of the enzyme. In other preferred embodiments, an expression vector is used to transfer the cDNA into a suitable cell or cell line for expression thereof. In one particularly preferred embodiment, the cDNA is transfected into a Chinese Hamster Ovary (CHO) cell, such as the CHO-K1 cell line. In yet other preferred embodiments, the production procedure comprises the following steps: (a) growing cells transfected with a DNA encoding all or a biologically active fragment or mutant of a human N-acetylgalactosamine-4-sulfatase in a suitable growth medium to an appropriate density, (b) introducing the transfected cells into a bioreactor, (c) supplying a suitable growth medium to the bioreactor, and (d) separating the transfected cells from the media containing the enzyme.

In a fourth aspect, the present invention provides a transfected cell line which features the ability to produce N-acetylgalactosamine-4-sulfatase (ASB) in amounts which enable using the enzyme therapeutically. In a preferred embodiment, the N-acetylgalactosamine-4-sulfatase is precursor N-acetylgalactosamine-4-sulfatase. In preferred embodiments, the present invention features a recombinant CHO cell line such as the CHO K1 cell line that stably and reliably produces amounts of an N-acetylgalactosamine-4-sulfatase (ASB) or a biologically active fragment, mutant or analog thereof which enable using the enzyme therapeutically. Especially preferred is the transgenic CHO-K1 cell line designated CSL4-S342. In some preferred embodiments, the transgenic cell line contains one or more copies of an expression construct. Preferably, the transgenic cell line contains about 10 or more copies of the expression construct. In even more preferred embodiments, the cell line expresses the recombinant N-acetylgalactosamine-4-sulfatase (ASB) or a biologically active fragment, mutant or analog thereof in amounts of at least about 20–40 micrograms per $10^7$ cells per day.

In a fifth aspect, the present invention provides novel vectors suitable to produce N-acetylgalactosamine-4-sulfatase (ASB) or a biologically active fragment, mutant or analog thereof in amounts which enable using the enzyme therapeutically.

In a sixth aspect, the present invention provides novel N-acetylgalactosamine-4-sulfatase (ASB) or a biologically active fragment, mutant or analog thereof produced in accordance with the methods of the present invention and thereby present in amounts which enable using the enzyme therapeutically. The specific activity of the N-acetylgalactosamine-4-sulfatase (ASB) according to the present invention is preferably in the range of 20–90 units, and more preferably greater than about 50 units per mg protein. In the preferred embodiment, the N-acetylgalactosamine-4-sulfatase is highly purified precursor N-acetylgalactosamine-4-sulfatase.

In a seventh aspect, the present invention features a novel method to purify N-acetylgalactosamine-4-sulfatase (ASB) or a biologically active fragment, mutant or analog thereof. According to a first embodiment, a transfected cell mass is grown and removed leaving recombinant enzyme. Exogenous materials should normally be separated from the crude bulk to prevent fouling of the columns. Preferably, the growth medium containing the recombinant enzyme is passed through an ultrafiltration step. In another preferred embodiment, the method to purify the precursor N-acetylgalactosamine-4-sulfatase comprises: (a) obtaining a fluid containing precursor N-acetylgalactosamine-4-sulfatase; (b) reducing the proteolytic activity of a protease in said fluid able to cleave the precursor N-acetylgalactosamine-4-sulfatase, wherein said reducing does not harm said precursor N-acetylgalactosamine-4-sulfatase; (c) contacting the fluid with a Cibracon blue dye interaction chromatography resin; (d) contacting the fluid with a copper chelation chromatography resin; (e) contacting the fluid with a phenyl hydrophobic interaction chromatography resin; (f) recovering said precursor N-acetylgalactosamine-4-sulfatase. Preferably, steps (c), (d) and (e) can be performed sequentially. Those skilled in the art readily appreciate that one or more of the chromatography steps may be omitted or substituted, or that the order of the chromatography steps may be changed within the scope of the present invention. In other preferred embodiments, the eluent from the final chromatography column is ultrafiltered/diafiltered, and an appropriate step is performed to remove any remaining viruses. Finally, appropriate sterilizing steps may be performed as desired.

DESCRIPTION OF THE FIGURES

FIGS. 6A–6F depict the results on 4–20% polyacrylamide gradient SDS gels of the following samples: lane 1, NEB broad range prestained molecule weight standards (MW in kDa); lane 2, 5 µg ASB from lot AS60001 (old batch process); lane 3, 5 µg ASB from lot AP60109 UF4 (perfusion process); lane 4, 5 µg ASB from lot AP60109 UF10 (perfusion process); lane 5, 5 µg ASB from lot AP60109 UF15 (perfusion process); lane 6, 5 µg ASB from lot AP60109 AUF18 (perfusion process); lane 7, 5 µg ASB from lot AP60109 AUF22 (perfusion process); lane 8, 5 µg ASB from lot AP60109 AUF25 (perfusion process); and, lane 9, 5 µg ASB from lot AP60109 AUF27 (perfusion process). The gels are stained either with Coomassie R-250 or silver-stained.

FIGS. 8A–8C depicts profiles obtained for the Blue Sepharose Column (FIG. 8A), Copper Chelating Sepharose Column (FIG. 8B) and Phenyl Sepharose Column (FIG. 8C). In FIG. 8B, cathepsin activity is indicated by the red line.

DETAILED DESCRIPTION OF THE INVENTION

Figure 1:
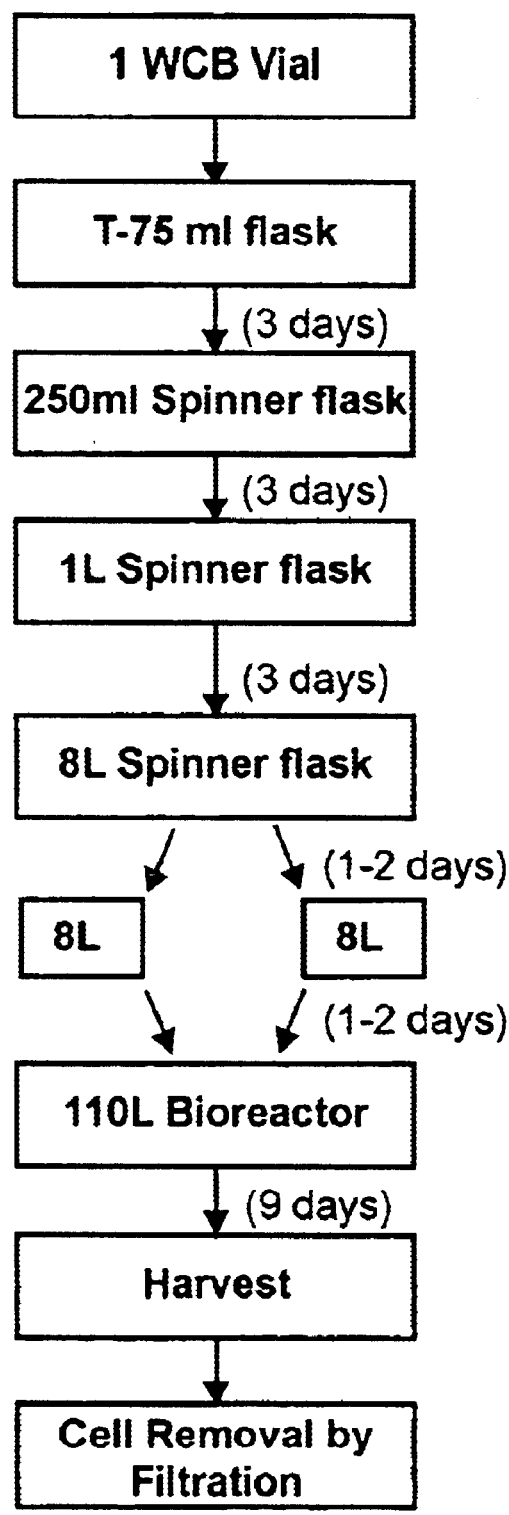
FIG. 1 provides a flow diagram of the method for producing a human N-acetylgalactosamine-4-sulfatase (ASB) according to the present invention.

The present invention encompasses the production, purification, and the use of a composition comprising a highly purified N-acetylgalactosamine-4-sulfatase in the precursor form. The purity of N-acetylgalactosamine-4-sulfatase in the precursor form is at least equal to or greater than 95, 96, 97 or 98% by total protein as determined by the reverse-phase HPLC method. Preferably, the purity is at least equal to or greater than 99%. More preferably, the purity is at least equal to or greater than 99.1, 99.2, 99.3 or 99.4%. Even more preferably, the purity is at least equal to or greater than 99.5, 99.6, 99.7 or 99.8%. Even much more preferably, the purity is at least equal to or greater than 99.9%. The purity of precursor N-acetylgalactosamine-4-sulfatase is measured using the reverse-phase HPLC method (see Example 9). The purity of precursor N-acetylgalactosamine-4-sulfatase is that whereby the composition essential free of any contaminating cell proteins or degraded or mature or processed N-acetylgalactosamine-4-sulfatase that is detectable by the reverse-phase HPLC method. All percent purity is based on total protein as determined by the reverse-phase HPLC method.

In a first aspect, the present invention features novel methods of treating diseases caused all or in part by a deficiency in N-acetylgalactosamine-4-sulfatase (ASB). In one embodiment, this method features administering a recombinant N-acetylgalactosamine-4-sulfatase (ASB) or a biologically active fragment, mutant or analog thereof alone or in combination with a pharmaceutically suitable carrier. In other embodiments, this method features transferring a nucleic acid encoding, all or a part of an N-acetylgalactosamine-4-sulfatase (ASB) or a biologically active mutant thereof into one or more host cells in vivo. Preferred embodiments include optimizing the dosage to the needs of the organism to be treated, preferably mammals or humans, to effectively ameliorate the disease symptoms. In preferred embodiments the disease is mucopolysaccharidosis VI (MPS VI), Maroteaux-Lamy syndrome.

The purity of precursor N-acetylgalactosamine-4-sulfatase is that whereby the composition is essentially free of any contaminating cell proteins which can cause an immunological or allergic reaction by the subject who is administered precursor N-acetylgalactosamine-4-sulfatase. A composition is essentially free of such contaminating cell proteins if the composition, when administered to a subject, does not cause any immunological or allergic reaction. The high purity of the precursor N-acetylgalactosamine-4-sulfatase is important for avoiding an immunological or allergic reaction by the subject to the impurities present in the pharmaceutical composition. This is especially true of proteins of the cells from which the precursor N-acetylgalactosamine-4-sulfatase is purified. When recombinant precursor N-acetylgalactosamine-4-sulfatase is expressed and purified from Chinese Hamster Ovary cells, the Chinese Hamster Ovary proteins can cause immunological or allergic reactions (e.g. hives) in the subject. The only means to avoid this type of reaction is ensure that the precursor N-acetylgalactosamine-4-sulfatase is sufficiently pure so that the contaminating Chinese Hamster Ovary proteins are not of sufficient amount to cause such reaction (s). The purity of the pharmaceutical composition is especially important as subjects include patients suffering from MPS VI and are thus already immunologically compromised.

The indication for recombinant human N-acetylgalactosamine-4-sulfatase (rhASB) is for the treatment of MPS VI, also known as Maroteaux-Lamy Syndrome. According to preferred embodiments, an initial dose of 1 mg/kg (~50 U/kg) is provided to patients suffering from a deficiency in N-acetylgalactosamine-4-sulfatase. Preferably, the N-acetylgalactosamine-4-sulfatase is administered weekly by injection. According to other preferred embodiments, patients who do not demonstrate a reduction in urinary glycosaminoglycan excretions of at least fifty percent are changed to a dosage of 2 mg/kg (~100 U/kg) within about three months of initial dosage. Preferably, the N-acetylgalactosamine-4-sulfatase (rhASB) or a biologically active fragment, mutant or analog thereof is administered intravenously over approximately a four-hour period once weekly preferably for as long as significant clinical symptoms of disease persist. Also, preferably, the N-acetylgalactosamine-4-sulfatase (rhASB) is administered by an intravenous catheter placed in the cephalic or other appropriate vein with an infusion of saline begun at about 30 cc/hr. Further, preferably the N-acetylgalactosamine-4-sulfatase (rhASB) is diluted into about 100 cc of normal saline supplemented with about 1 mg/ml human albumin.

In a second aspect, the present invention features novel pharmaceutical compositions comprising human N-acetylgalactosamine-4-sulfatase (rhASB) or a biologically active fragment, mutant or analog thereof useful for treating a deficiency in N-acetylgalactosamine-4-sulfatase. The recombinant enzyme may be administered in a number of ways in addition to the preferred embodiments described above, such as parenteral, topical, intranasal, inhalation or oral administration. Another aspect of the invention is to provide for the administration of the enzyme by formulating it with a pharmaceutically-acceptable carrier which may be solid, semi-solid or liquid or an ingestable capsule. Examples of pharmaceutical compositions include tablets, drops such as nasal drops, compositions for topical application such as ointments, jellies, creams and suspensions, aerosols for inhalation, nasal spray, liposomes. Usually the recombinant enzyme comprises between 0.05 and 99% or between 0.5 and 99% by weight of the composition, for example between 0.5 and 20% for compositions intended for injection and between 0.1 and 50% for compositions intended for oral administration.

To produce pharmaceutical compositions in this form of dosage units for oral application containing a therapeutic enzyme, the enzyme may be mixed with a solid, pulverulent carrier, for example lactose, saccharose, sorbitol, mannitol, a starch such as potato starch, corn starch, amylopectin, laminaria powder or citrus pulp powder, a cellulose derivative or gelatine and also may include lubricants such as magnesium or calcium stearate or a Carbowax or other polyethylene glycol waxes and compressed to form tablets or cores for dragees. If dragees are required, the cores may be coated for example with concentrated sugar solutions which may contain gum arabic, talc and/or titanium dioxide, or alternatively with a film forming agent dissolved in easily volatile organic solvents or mixtures of organic solvents. Dyestuffs can be added to these coatings, for example, to distinguish between different contents of active substance. For the composition of soft gelatine capsules consisting of gelatine and, for example, glycerol as a plasticizer, or similar closed capsules, the active substance may be admixed with a Carbowax or a suitable oil as e.g., sesame oil, olive oil, or arachis oil. Hard gelatine capsules may contain granulates of the active substance with solid, pulverulent carriers such as lactose, saccharose, sorbitol, mannitol, starches such as potato starch, corn starch or amylopectin, cellulose derivatives or gelatine, and may also include magnesium stearate or stearic acid as lubricants.

Therapeutic enzymes of the present invention may also be administered parenterally such as by subcutaneous, intramuscular or intravenous injection either by single injection or pump infusion or by sustained release subcutaneous implant, and therapeutic enzymes may be administered by inhalation. In subcutaneous, intramuscular and intravenous injection the therapeutic enzyme (the active ingredient) may be dissolved or dispersed in a liquid carrier vehicle. For parenteral administration the active material may be suitably admixed with an acceptable vehicle, preferably of the vegetable oil variety such as peanut oil, cottonseed oil and the like. Other parenteral vehicles such as organic compositions using solketal, glycerol, formal, and aqueous parenteral formulations may also be used.

For parenteral application by injection, compositions may comprise an aqueous solution of a water soluble pharmaceutically acceptable salt of the active acids according to the invention, desirably in a concentration of 0.5–10%, and optionally also a stabilizing agent and/or buffer substances in aqueous solution. Dosage units of the solution may advantageously be enclosed in ampoules.

When therapeutic enzymes are administered in the form of a subcutaneous implant, the compound is suspended or dissolved in a slowly dispersed material known to those skilled in the art, or administered in a device which slowly releases the active material through the use of a constant driving-force such as an osmotic pump. In such cases administration over an extended period of time is possible.

For topical application, the pharmaceutical compositions are suitably in the form of an ointment, cell, suspension, cream or the like. The amount of active substance may vary, for example between 0.05–20% by weight of the active substance. Such pharmaceutical compositions for topical application may be prepared in known manner by mixing, the active substance with known carrier materials such as isopropanol, glycerol, paraffin, stearyl alcohol, polyethylene glycol, etc. The pharmaceutically acceptable carrier may also include a known chemical absorption promoter. Examples of absorption promoters are, e.g., dimethylacetamide (U.S. Pat. No. 3,472,931), trichloro ethanol or trifluoroethanol (U.S. Pat. No. 3,891,757), certain alcohols and mixtures thereof (British Patent No. 1,001,949). A carrier material for topical application to unbroken skin is also described in the British patent specification No. 1,464,975, which discloses a carrier material consisting of a solvent comprising 40–70% (v/v) isopropanol and 0–60% (v/v) glycerol, the balance, if any, being an inert constituent of a diluent not exceeding 40% of the total volume of solvent.

The dosage at which the therapeutic enzyme containing pharmaceutical compositions are administered may vary within a wide range and will depend on various factors such as for example the severity of the disease, the age of the patient, etc., and may have to be individually adjusted. As a possible range for the amount of therapeutic enzyme which may be administered per day be mentioned from about 0.1 mg- to about 2000 mg or from about 1 mg to about 2000 mg.

The pharmaceutical compositions containing the therapeutic enzyme may suitably be formulated so that they provide doses within these ranges either as single dosage units or as multiple dosage units. In addition to containing a therapeutic enzyme (or therapeutic enzymes), the subject formulations may contain one or more substrates or cofactors for the reaction catalyzed by the therapeutic enzyme in the compositions. Therapeutic enzyme containing, compositions may also contain more than one therapeutic enzyme. Likewise, the therapeutic enzyme may be in conjugate form being bound to another moiety, for instance PEG. Additionally, the therapeutic enzyme may contain one or more targeting moieties or transit peptides to assist delivery to a tissue, organ or organelle of interest.

The recombinant enzyme employed in the subject methods and compositions may also be administered by means of transforming patient cells with nucleic acids encoding the N-acetylgalactosamine-4-sulfatase or a biologically active fragment, mutant or analog thereof. The nucleic acid sequence so encoding may be incorporated into a vector for transformation into cells of the patient to be treated. Preferred embodiments of such vectors are described herein. The vector may be designed so as to integrate into the chromosomes of the subject, e.g., retroviral vectors, or to replicate autonomously in the host cells. Vectors containing encoding N-acetylgalactosamine-4-sulfatase nucleotide sequences may be designed so as to provide for continuous or regulated expression of the enzyme. Additionally, the genetic vector encoding the enzyme may be designed so as to stably integrate into the cell genome or to only be present transiently. The general methodology of conventional genetic therapy may be applied to polynucleotide sequences encoding- N-acetylgalactosamine-4-sulfatase. Reviews of conventional genetic therapy techniques can be found in Friedman, *Science* 244:1275–1281 (1989); Ledley, *J. Inherit. Aletab. Dis.* 13:587–616 (1990); and, Tososhev, et al., *Curr. Opinions Biotech.* 1:55–61 (1990).

A particularly preferred method of administering the recombinant enzyme is intravenously. A particularly preferred composition comprises recombinant N-acetylgalactosamine-4-sulfatase, normal saline, phosphate buffer to maintain the pH at about 5–7, and human albumin. The composition may additionally include polyoxyethylenesorbitan 20 or 80 (Tween-20 or Tween-80) to improve the stability and prolong shelf life. These ingredients may be provided in the following amounts:

| | |
|---|---|
| N-acetylgalactosamine-4-sulfatase | 1–5 mg/ml or 50–250 units/ml |
| Sodium chloride solution | 150 mM in an IV bag, 50–250 cc total volume |
| Sodium phosphate buffer | 10–100 mM, pH 5.8 |
| Human albumin | 1 mg/mL |
| Tween –20 or Tween –80 | 0.001% (w/v) |

In a third aspect, the present invention features a method to produce N-acetylgalactosamine-4-sulfatase (ASB) or a biologically active fragment, mutant or analog thereof in amounts which enable using the enzyme therapeutically. In a broad embodiment, the method comprises the step of transfecting a cDNA encoding for all or a part of a N-acetylgalactosamine-4-sulfatase (ASB) or a biologically active mutant or analog thereof into a cell suitable for the expression thereof. In some embodiments, a cDNA encoding for a complete N-acetylgalactosamine-4-sulfatase (ASB) is used, preferably a human N-acetylgalactosamine-4-sulfatase (ASB). However, in other embodiments, a cDNA encoding for a biologically active fragment or mutant thereof may be used. Specifically, one or more amino acid substitutions may be made while preserving or enhancing the biological activity of the enzyme.

In other preferred embodiments, an expression vector is used to transfer the cDNA into a suitable cell or cell line for expression thereof. In one particularly preferred embodiment, the cDNA is transfected into a Chinese hamster ovary cell, such as the CHO-K1 cell line. In yet other preferred embodiments, the production procedure comprises the following steps: (a) growing cells transfected with a DNA encoding all or a biologically active fragment or mutant of a human N-acetylgalactosamine-4-sulfatase a suitable growth medium to an appropriate density, (b) introducing the transfected cells into a bioreactor, (c) supplying a suitable growth medium to the bioreactor, (d) harvesting said medium containing the recombinant enzyme, and (e) substantially removing the transfected cells from the harvest medium.

A suitable medium for growing the transfected cells is a JRH Excell 302 medium supplemented with L-glutamine, glucose and hypoxanthine/thymidine in addition to G418. In a preferred medium, the JRH Excell 302 medium is further supplemented with folic acid, serine, and asparagine, and there is no G418 present in the medium. Using this preferred medium to culture cells provides a higher purity precursor rhASB compared to using the medium supplemented with G418 but not with folic acid, serine, and asparagine (see lane 2 of FIG. 6). It is preferred to grow the cells in such a medium to achieve a cell density of about $1 \times 10^7$ cells/ml resulting in 10–40 mg/ml of active enzyme. Moreover, it is preferable to grow the transfected cells in a bioreactor for about 5 to 15 days. More preferably, it is about 9 days. Preferably, the transfected cells are grown in a bioreactor using a perfusion-based process with collections continuing up to 35 days. More preferably, the transfected cells are grown in a bioreactor using a perfusion-based process with collections continuing up to 45 days. Even more preferably, the transfected cells are grown in a bioreactor using a perfusion-based process with collections continuing up to 60 days. Even much more preferably, the transfected cells are grown in a bioreactor using a perfusion-based process with collections continuing up to 90 days.

According to preferred embodiments, the transfected cells may be substantially removed from the bioreactor supernatant by filtering them through successive membranes such as a 10 μm membrane followed by a 1 μm membrane followed by a 0.2 μm. Any remaining harvest medium may be discarded prior to filtration.

Recombinant human N-acetylgalactosamine-4-sulfatase may be produced in Chinese hamster ovary cells (Peters, et al. *J. Biol. Chem.* 265:3374–3381). Its uptake is mediated by a high affinity mannose-6-phosphate receptor expressed on most, if not all, cells (Neufeld et al., "The mucopolysaccharidoses" *The Metabolic Basis of Inherited Disease*, eds. Scriver, et al. New York: McGraw-Hill (1989) p. 1565–1587). Once bound to the mannose-6-phosphate receptor, the enzyme is endocytosed through coated pits and transported to the lysosomes. At the pH of lysosomes, the enzyme is active and begins removing sulfate residues from accumulated dermatan sulfate. In MPS VI fibroblasts, the clearance of storage is rapid and easily demonstrated within 92 hours of enzyme exposure (Anson, et al., *J. Clin. Invest.* 99:651–662 (1997)). The recombinant enzyme may be produced at a 110-L (approximately 90 L working volume) fermentation scale according to a process according to the flow diagram outlined in FIG. 1.

The recombinant enzyme can be produced using the following method as set forth in Table 1A–C.

TABLE 1A

Cell Culture Process by the Fed Batch Process

| Step | Process | In-Process Testing |
|---|---|---|
| 1. Thawing of the Working Cell Bank (WCB) | Inoculate the thawed cells into one T-75 flask with 25 mL of JRH Exell 302 medium supplemented with 4 mM L-glutamine, 4.5 g/L glucose and 10 mg/L hypoxanthine/thymidine; further supplemented with folic acid, serine and asparagine (no G418) Culture for 3 days to achieve $1 \times 10^{10}$ cell density ↓ | Cell count Cell viability |
| 3. 250 mL Spinner Flask | Add cells to 175 mL of supplemented medium (no G418) Culture for 3 days ↓ | Cell count Cell viability |
| 4. 1 L Spinner Flask | Add cells to 800 mL of supplemented medium (no G418) Culture for 1–2 days ↓ | Cell count Cell viability |

TABLE 1A-continued

Cell Culture Process by the Fed Batch Process

| Step | Process | In-Process Testing |
|---|---|---|
| 5. 8 L Spinner Flask | Add cells to 4 L of supplemented medium (no G418) Culture for 1–2 days ↓ | Cell count Cell viability |
| 6. 2 × 8 L Spinner Flask | Split working volume into 2 8 L Spinner Flasks Add cells to 5.5 L of supplemented medium (no G418) to each 8 L Spinner Flask Culture for 1–2 days ↓ | Cell count Cell viability |
| 7. Inoculation of 110 L Bioreactor | Add cells to 7 mL of supplemented medium Culture 9 days ↓ | Cell count Cell viability |
| 8. Production | Approximately 9 days of growth in bioreactor ↓ | Cell Count Cell viability Activity |
| 9. Harvest Supernatant | Harvest is pumped into 100 L bag, refrigerated overnight ↓ | |
| 10. Cell Removal | Cells are removed from the harvest medium by filtration through a 10 μm membrane cartridge followed by 1 μm and 0.2 μm cartridges. Since the cells have been allowed to settle overnight the final 5 to 10% of the harvest medium is discarded prior to filtration. | QC Release Point Activity Bioburden Endotoxin Mycoplasma In vitro advent. Agents |

In one embodiment, the transfected cells are grown in a cell culture process that is a perfusion-based process with collections continuing for up to 35 or more days with a collection rate of approximately 400 L per day from one 110 L bioreactor. Preferably, the collection rate is approximately 800 L per day from one 110 L bioreactor. A process flow diagram comparing the perfusion cell culture process with the batch cell culture process is shown in Table 1B. Comparisons to the fed batch process as well as details of the specific changes implemented for the perfusion-based cell culture process are summarized in Table 1C.

TABLE 1B

Cell Culture Process Comparison Between Fed Batch and Perfusion Processes

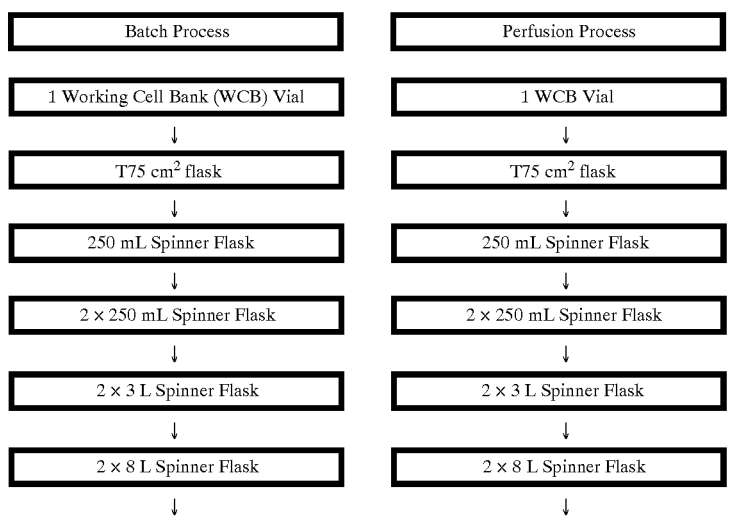

TABLE 1B-continued

Cell Culture Process Comparison Between Fed Batch and Perfusion Processes

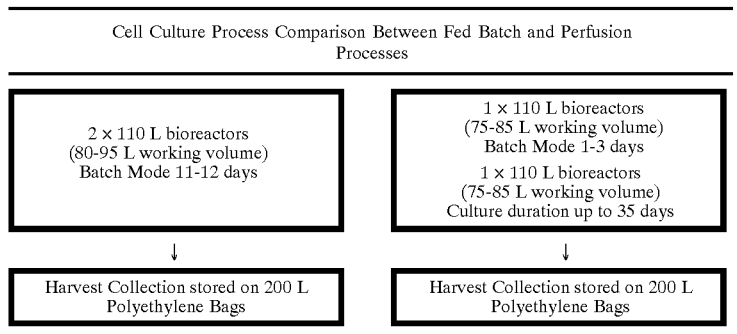

TABLE 1C

Summary Description of the Differences between the Fed Batch and Perfusion Processes

| Production Step | Description (Batch) | Description (Perfusion) |
|---|---|---|
| CELL CULTURE | One batch is the result of one production run with two 110 L bioreactors. | Change: One batch is the result of one production run with one 110 L bioreactor |
| Thawing of WCB vial | One vial for each production batch. Tests: Expected cell viability >95% Expected $\geq 1 \times 10^6$ cells recovered | Change: Cell Viability: >90% Viability of >90% on thaw has proven to yield successful runs and product that meets specifications |
| T75 cm$^2$ flasks | Approximately $5 \times 10^6$ cells plated into 1 flask. Length of step: ~3 days Tests: Expected cell viability >90% Expected $\geq 2 \times 10^7$ cells recovered | No Change |
| 250 mL Spinner Flask | Cells from T75 is split onto a 250 mL spinner flask. Length of step: ~2 days Tests: Expected cell viability >90% Expected $\geq 2 \times 10^8$ cells recovered | No Change |
| 2 × 250 mL Spinner Flask | Cells from 1 × 250 mL spinner flask are split into two 250 mL spinner flask. Length of step: ~3 days Tests: Expected cell viability >90% Expected $\geq 4 \times 10^8$ cells recovered | No Change |
| 2 × 3 L Spinner Flask | Cells from 2 × 250 mL spinner flasks are split into two 3 L spinner flask Length of step: ~4 days Tests: Expected cell viability >90% Expected $\geq 4.8 \times 10^9$ cells recovered | No Change |
| 2 × 8 L Spinner Flask | Cells from 2 × 3 L spinner flasks are split into two 8 L spinner flask. Length of step: ~2 days Tests: Expected cell viability >90% Expected $\geq 1.6 \times 10^{10}$ cells recovered | No Change |
| Inoculation of culture flask | Inoculum of $\geq 0.8 \times 10^{10}$ cells are added to each of two bioreactors containing 32 L culture medium each. Culture monitored with PC-interfaced control system. | Change: Inoculum of $\geq 1.6 \times 10^{10}$ cells added to one bioreactor containing 64 L culture medium. (Reflects the use of one bioreactor versus two.) |
| Production | Growth: 3 days of growth until culture reaches density of $>3.2 \times 10^{10}$ cells. Vertical Split: Culture media added to final volume of 95 L. Harvesting: Supernatant was harvested at day 11 or when cell viability fell | Changes: Growth/Transition/Harvesting: When cell density reaches $>8 \times 10^{10}$ cells/mL, perfusion is started. The perfusion rate is gradually increased to 5 vessel |

TABLE 1C-continued

Summary Description of the Differences between the
Fed Batch and Perfusion Processes

| Production Step | Description (Batch) | Description (Perfusion) |
|---|---|---|
| | below 70%. Supernatant is filtered and stored. | volumes per day based on glucose levels. When the cell density is >1.28 × $10^{12}$ the pH set point is adjusted to 7.35. Once increases in perfusion rates cease, glucose level is maintained by reducing cell density with a cell bleed. Harvested supernatant is collected and filtered. |
| Termination | Run is terminated at harvest. | Change: Run is terminated after 35 or more days is reached, or activity falls below 2 mg/L for three consecutive days or after adequate harvested supernatant is collected. |

The inoculum preparation for scale-up process is the same for the fed batch and perfusion processes. In one embodiment, the rhASB cell culture is initiated by thawing a single vial from the Working Cell Bank and transferring its contents (approximately 1 mL) to approximately 25 mL of EX-CELL 302 Medium (Modified w/L-Glutamine, No Phenol Red) in a T75 $cm^2$ cell culture flask. In each expansion step, the cell culture is incubated until a viable cell count of approximately $0.8 \times 10^6$ cells/mL is achieved. Each cell expansion step is monitored for cell growth (cell density) and viability (via trypan blue exclusion). All additions of EX-CELL 302 Medium (Modified w/L-Glutamine, No Phenol Red) medium and cell transfers are preformed aseptically in a laminar flow hood. The cell culture is expanded sequentially from the T75 $cm^2$ flask to a 250 mL spinner flask, to two 250 mL spinner flasks, to two 3 L spinner flasks, and finally to two 8 L spinner flasks. The entire scale-up process lasts approximately 14 days. When the two 8 L spinner flasks are at a density of at least $1.0 \times 10^6$ cells/mL, the flasks are used to seed one 110 L bioreactor.

It is preferred that bioreactor operations for rhASB expression or production or manufacture utilize a perfusion-based cell culture process. Preferably, the bioreactor, using the perfusion process, can control cell densities up to as high as 37 million cells per mL; compared to 4–5 million cells per mL using the fed batch process.

The perfusion-based process runs longer (35 days) than the fed batch process (11–12 days) and produces a greater volume of harvested cell culture fluid (approximately 400 L/day at a perfusion rate of 5 vessel volumes per day) compared to the fed batch process (190 L/run). Preferably, harvesting is performed up to 35 days for a total collection of approximately 8400 L of supernatant.

End of Production Cells (EPC) are evaluated for genetic stability, identity, sterility and adventitious agent contamination per ICH guideline. Preferably, EPC results, obtained from a 35-day long bioreactor run, AC60108, produced under cGMP conditions, show no growth or negative results or no detection of the presence of bacteria and fungi, mycoplasma, adventitious viral contaminants, murine viruses, or like contaminants or particles.

In a fourth aspect, the present invention provides a transgenic cell line which features the ability to produce N-acetylgalactosamine-4-sulfatase (ASB) or a biologically active fragment, mutant or analog thereof in amounts which enable using the enzyme therapeutically. In preferred embodiments, the present invention features a recombinant Chinese hamster ovary cell line such as the CHO K1 cell line that stably and reliably produces amounts of N-acetylgalactosamine-4-sulfatase (ASB) which enable using the enzyme therapeutically. Especially preferred is the CHO-K1 cell line designated CSL4S-342. In some preferred embodiments, the cell line contains one or more of an expression construct. More preferably, the cell line contains contains about 10 or more copies of the expression construct. In even more preferred embodiments, the cell line expresses recombinant N-acetylgalactosamine-4-sulfatase (ASB) in amounts of at least about 40–80 micrograms per $10^7$ cells per day.

Recombinant human N-acetylgalactosamine-4-sulfatase (rhASB) may be produced from a stable transfected CHO-K1 (Chinese hamster ovary) cell line designated CSL4S-342. The cell line is described in the literature (Crawley, J. Clin. Invest. 99:651–662 (1997)). Master Cell Bank (MCB) and Working Cell Bank (WBC) were prepared at Tektagen Inc. (Malvern, Pa.). The cell banks have been characterized per ICH recommended guidelines for a recombinant mammalian cell line.

In a fifth aspect, the present invention provides novel vectors suitable to produce N-acetylgalactosamine-4-sulfatase (ASB) or a biologically active fragment, mutant or analog thereof in amounts which enable using the enzyme therapeutically.

In a sixth aspect, the present invention provides novel N-acetylgalactosamine-4-sulfatase (ASB) or a biologically active fragment, mutant or analog thereof produced in accordance with the methods of the present invention and thereby present in amounts which enable using the enzyme therapeutically. The preferred specific activity of the N-acetylgalactosamine-4-sulfatase (ASB) according to the present invention is about 20–90 Unit, and more preferably greater than 50 units per milligram protein. Preferably, the enzyme has a deglycosylated weight of about 55 to 56 kDa, most preferably about 55.7 kDa. Preferably, the enzyme has a glycosylated weight of about 63 to 68 kDa, most preferably about 64 to 66 kDa. The present invention also includes biologically active fragments including truncated molecules, analogs and mutants of the naturally-occurring human N-acetylgalactosamine-4-sulfatase.

The human cDNA for N-acetylgalactosamine-4-sulfatase predicts a protein of 533 amino acids with a signal peptide of 41 amino acids (Peters, et al. *J. Biol. Chem.* 265:3374–3381). The predicted molecular weight is about 55.9 kDa after signal peptide cleavage. The recombinant enzyme has an apparent molecular weight of 64 kDa on SDS-PAGE due to carbohydrate modifications. The predicted protein sequence contains six potential N-linked oligosaccharide modification sites of which four may be used based on a 2,000 kDa average mass and 8,000 kDa difference between predicted and apparent mass. A mature form of the intracellular protein has three peptides attached by cystine bonds. The largest peptide has a molecular weight of 47 kDa; the other two has a molecular weight of 6 and 7 kDa respectively.

A description of a drug product produced and purified according to the methods of the present invention is provided in Table 2.

TABLE 2

Drug Product Preliminary Specifications

| Test | Procedure | Specification |
| --- | --- | --- |
| Activity | Fluorescence assay | 20,000–120,000 mUnits |
| Adventitious Viruses* | In Vitro Assay | Pass |
| Appearance | Visual | Clear, colorless to pale yellow solution |
| Bacterial Endotoxin | LAL | ≦2 EU/mL |
| Chloride | Atomic Absorption | Report Value |
| ASB fibroblast Uptake Assay | TBD | ≦40 nmol |
| Mycoplasma* | Points to Consider 1993 | Pass |
| Particulates | USP | ≦600/vial at 25 μm & ≦6000/vial at 10 μm |
| PH | USP | 5.5–6.8 |
| Phosphate | Atomic Absorption | Report Value |
| Protein Concentration | UV 280 | 0.8–1.2 mg/ml |
| Purity | SDS PAGE | 1 major band between 65–70 kDa |
| | RP-HPLC | >95% |
| Residual Blue Dye | TBD | Report Value |
| Residual Copper | TBD | Report Value |
| Sodium | Atomic Absorption | Report Value |
| Specific Activity | Calculation | 40,000–80,000 mUnits/mg |
| Sterility | 21 CFR 610 | Pass |

*Tested on harvested supernatant from bioreactor (after cell removal by filtration).

Figure 2:
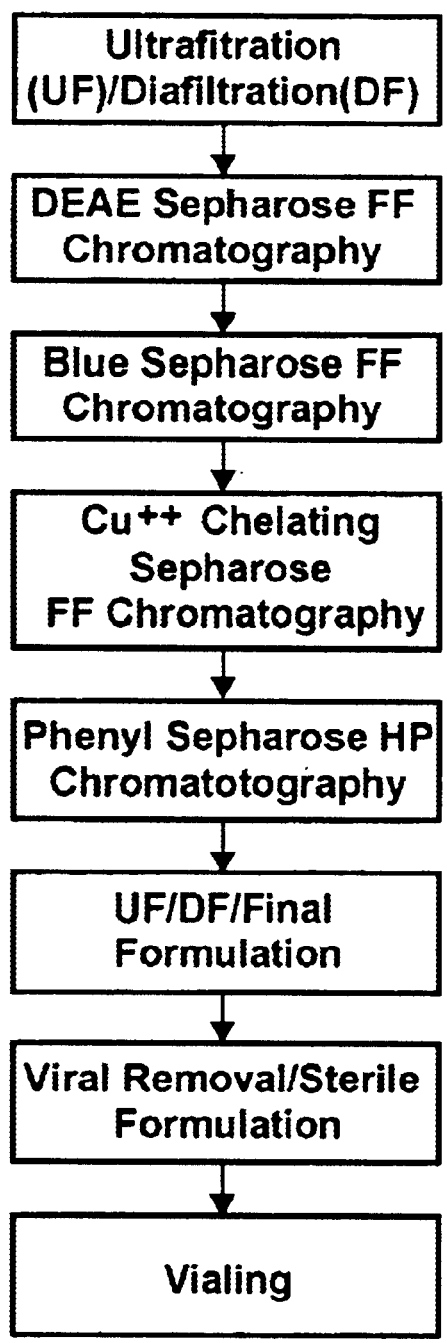
FIG. 2 provides a flow diagram of the method for purifying a human N-acetylgalactosamine-4-sulfatase (ASB) according to the batch process method (Table 14).

In a seventh aspect, the present invention features a novel method to purify N-acetylgalactosamine-4-sulfatase (ASB) or a biologically active fragment, mutant or analog thereof. According to a first embodiment, a transfected cell mass is grown and removed leaving recombinant enzyme. Exogenous materials should normally be separated from the crude bulk to prevent fouling of the columns. Preferably, the growth medium containing the recombinant enzyme is passed through an ultrafiltration and diafiltration step. In one method, the filtered solution is passed through a DEAE Sepharose chromatography column, then a Blue Sepharose chromatography column, then a Cu++ Chelating Sepharose chromatography column, and then a Phenyl Sepharose chromatography column. Such a four step column chromatography including using a DEAE Sepharose, a Blue Sepharose, a Cu++ Chelating Sepharose and a Phenyl Sepharose chromatography column sequentially results in especially highly purified recombinant enzyme. Those of skill in the art appreciate that one or more chromatography steps may be omitted or substituted or the order of the steps altered within the scope of the present invention. In other preferred embodiments, the eluent from the final chromatography column is ultrafiltered/diafiltered, and an appropriate step is performed to remove any remaining viruses. Finally, appropriate sterilizing steps may be performed as desired. The recombinant enzyme may be purified according to a process outlined in FIG. 2. The quality of the recombinant enzyme is key to patients. The rhASB produced by this method is substantially pure (>95%).

In a preferred embodiment, the ultrafiltration/diafiltration step is performed with a sodium phosphate solution of about 10 mM and with a sodium chloride solution of about 100 mM at a pH of about 7.3. In another embodiment, the DEAE Sepharose chromatography step is performed at a pH of about 7.3 wherein the elute solution is adjusted with an appropriate buffer, preferably a sodium chloride and sodium phosphate buffer. In additional preferred embodiments, the Blue Sepharose chromatography step is performed at a pH of about 5.5 wherein the elute solution is adjusted with an appropriate buffer, preferably a sodium chloride and sodium acetate buffer. Also, in preferred embodiments, the Cu++ Chelating Sepharose chromatography step is performed with an elution buffer including sodium chloride and sodium acetate. In especially preferred embodiments, a second ultrafiltration/diafiltration step is performed on the eluate from the chromatography runs wherein the recombinant enzyme is concentrated to a concentration of about 1 mg/ml in a formulation buffer such as a sodium chloride and sodium phosphate buffer to a pH of about 5.5 to 6.0, most preferably to a pH of 5.8. Phosphate buffer is a preferred buffer used in the process because phosphate buffer prevents critical degradation and improves the stability of the enzyme.

A more detailed description of particularly preferred purification methods within the scope of the present invention is set forth in Table 3.

TABLE 3

Purification Process Overview

| Step | Process | |
|---|---|---|
| 1. UF/DF | Filtered harvest fluid (HF) is concentrated ten fold and then diafiltered with 5 volumes of 10 mM Sodium Phosphate, 100 mM NaCl, pH 7.3 using a tangential flow filtration (TFF) system. | |
| 2. DEAE Sepharose FF (flow through) | Pre-wash 1 buffer: | 0.1 N NaOH |
| | Pre-wash 2 buffer: | 100 mM NaPO4 pH 7.3 |
| | Equilibration buffer: | 100 mM NaCl, 10 mM NaPO4, pH 7.3 |
| | Load: | Product from Step 1 |
| | Wash buffer: | 100 mM NaCl, 10 mM NaPO4, pH 7.3 |
| | Strip buffer: | 1 M NaCl, 10 mM NaPO4, pH 7.3 |
| | Sanitization buffer: | 0.5 N NaOH |
| | Storage buffer: | 0.1 N NaOH |
| 3. Blue Sepharose FF | Pre-wash 1: | 0.1 N NaOH |
| | Pre-wash 2: | $H_2O$ |
| | Pre-wash 3: | 1 M NaAc, pH 5.5 |
| | Equilibration buffer: | 150 mM NaCl, 20 mM NaAc, pH 5.5 |
| | Load: | DEAE flow through |
| | Wash buffer: | 150 mM NaCl, 20 mM NaAc, pH 5.5 |
| | Elution buffer: | 500 mM NaCl, 20 mM NaAc, pH 5.5 |
| | Regeneration buffer: | 1 M NaCl, 20 mM NaAc, pH 5.5 |
| | Sanitization buffer: | 0.1 N NaOH, 0.5–2 hours |
| | Storage buffer: | 500 mM NaCl, 20 mM NaAc, pH 5.5, 20% ETOH |
| 4. Cu++ Chelating Sepharose FF | Sanitization buffer: | 0.1 N NaOH |
| | Wash buffer: | $H_2O$ |
| | Charge Buffer: | 0.1 M Copper Sulfate |
| | Equilibration buffer: | 20 mM NaAc, 0.5 M NaCl, 10% Glycerol, pH 6.0 |
| | Load: | Blue Sepharose Eluate |
| | Wash Buffer 1: | 20 mM NaAc, 0.5 M NaCl, 10% Glycerol, pH 6.0 |
| | Wash Buffer 2: | 20 mM NaAc, 1 M NaCl, 10% Glycerol, pH 4.0 |
| | Wash Buffer 3: | 20 mM NaAc, 1 M NaCl, 10% Glycerol, pH 3.8 |
| | Elution Buffer: | 20 mM NaAc, 1 M NaCl, 10% Glycerol, pH 3.6 |
| | Strip Buffer: | 50 mM EDTA, 1 M NaCl |
| | Sanitization Buffer: | 0.5 N NaOH, 0.5–2 hours |
| | Storage Buffer: | 0.1 N NaOH |
| 5. Phenyl Sepharose HP | Pre-wash 1 Buffer: | 0.1 N NaOH |
| | Pre-wash 2 Buffer: | $H_2O$ |
| | Equilibration buffer: | 3 M NaCl, 20 mM NaAc, pH 4.5 |
| | Load: | $Cu^{++}$ Chelating Sepharose Eluate |
| | Wash Buffer 1: | 3.0 M NaCl, 20 mM NaAc, pH 4.5 |
| | Wash Buffer 2: | 1.5 M NaCl, 20 mM NaAc, pH 4.5 |
| | Elution buffer 1: | 1.0 M NaCl, 20 mM, NaAc, pH 4.5 |
| | Strip Buffer: | 0 M NaCl, 20 mM NaAc, pH 4.5 |
| | Sanitization Buffer: | 0.5 N NaOH |
| | Storage Buffer: | 0.1 N NaOH |
| 6. UF/DF | The purified rhASB is concentrated and diafiltered to a final concentration of 1.5 mg/ml in formulation buffer (150 mM NaCl, 10 mM NaPO4, pH 5.8) using a TFF system. | |
| 7. Formulation (if necessary) | Dilute with additional formulation buffer to 1.0 mg/ml | |
| 8. Viral Reduction/ Sterile filtration | 0.02 μm filtration into sterile container | |
| 9. Vialing | Product filled into 5 cc Type 1 glass vials, manually stoppered, crimped and labeled. | |

The formulated bulk drug substance can be sterilized through a 0.04 micron filter in a class 100 laminar flow hood into Type 1 glass vials. The vials may be filled to a final volume of about 5 mL using a semi-automatic liquid filling machine. The vials may then be manually stoppered, sealed and labeled.

A more preferred method to purify a precursor N-acetylgalactosamine-4-sulfatase comprises: (a) obtaining a fluid containing precursor N-acetylgalactosamine-4-sulfatase; (b) reducing the proteolytic activity of a protease in said fluid able to cleave the precursor N-acetylgalactosamine-4-sulfatase, wherein said reducing does not harm said precursor N-acetylgalactosamine-4-sulfatase; (c) contacting the fluid with a Cibracon blue dye interaction chromatography resin; (d) contacting the fluid with a copper chelation chromatography resin; (e) contacting the fluid with a phenyl hydrophobic interaction chromatography resin; and (f) recovering said precursor N-acetylgalactosamine-4-sulfatase. Preferable, steps (c), (d) and (e) are performed sequentially. This method requires no more than three chromatography steps or columns. In order to obtain highly purified precursor N-acetylgalactosamine-4-sulfatase, no further chromatography steps or columns are required. This method does not comprise the fluid contacting a DEAE Sepharose resin. The recovered precursor N-acetylgalactosamine-4-sulfatase has a purity of at least equal to or greater than 99%. The overall recovery yield can be at least about 40–60%.

Preferably, obtaining the fluid containing the precursor N-acetylgalactosamine-4-sulfatase comprises growing a culture of cells transformed with a gene encoding N-acetylgalactosamine-4-sulfatase; preferably, the gene encodes human N-acetylgalactosamine-4-sulfatase. Preferably, the cells are mammalian cells. More preferably, the mammalian cells are Chinese Hamster Ovary cells. The obtaining step can further comprise harvesting the fluid from said culture of cells. The obtaining step can further comprise concentrating said fluid to about 20x.

A feature of this method is an early separation of protease activity and the precursor N-acetylgalactosamine-4-sulfatase. This separation can comprise either (1) the reduction, inhibition, or inactivation of the protease activity, or (2) the physical separation of the protease(s) from the precursor N-acetylgalactosamine-4-sulfatase. Preferably, this separation occurs as early as possible during the purification process. The purpose is to keep to a minimum the number of molecules of precursor N-acetylgalactosamine-4-sulfatase being cleaved into the mature or processed form and/or other degraded form(s). The precursor form of N-acetylgalactosamine-4-sulfatase is the preferred form, as opposed to the mature or processed form, because it is more readily taken up into the target tissue and for subsequent targeting to the lysosome. The earlier or sooner the protease activity is separated from the precursor N-acetylgalactosamine-4-sulfatase: the fewer the number of molecules of the precursor form would be cleaved into the mature or processed form.

The activity of the protease is reduced or inhibited by adjusting the fluid to a pH value between about 4.8 to 8.0. Preferably, the pH value is between about 4.8 to 5.5. More preferably, the pH value is between about 4.8 and 5.2. The specific protease activity that is desired to be reduced is protease activity that specifically cleaves precursor form of N-acetylgalactosamine-4-sulfatase into the mature forms. The protease activity is found in one or more cysteine protease. A cysteine protease that specifically cleaves precursor N-acetylgalactosamine-4-sulfatase is cathepsin. This cathepsin has a molecular weight of about 36 kDa in its inactive form that is converted to its active forms of 21–29 kDa in size upon exposure to pH of less than 5.0 (see FIG. 9C). The pH can be adjusted into any value whereby the protease(s) is not converted from its inactive form to its active form and the desired precursor N-acetylgalactosamine-4-sulfatase, or biological activity thereof, is not harmed or not irreversibly harmed.

Preferably, step (c) comprises passing the fluid through a Cibracon blue dye interaction chromatography column. More preferably, the Cibracon blue dye interaction chromatography column is a Blue Sepharose 6 Fast Flow column. Preferably, step (d) comprises passing the fluid through a copper chelation chromatography column. More preferably, the copper chelation chromatography column is a Chelating Sepharose Fast Flow column. Preferably, step (e) comprises passing the fluid through a phenyl hydrophobic interaction chromatography column. More preferably, the phenyl hydrophobic interaction chromatography column is a Phenyl Sepharose 6 Fast Flow High Sub column. Preferably, the temporal sequence of steps (c), (d) and (e) is step (c), step (d) and step (e).

The recovering step can comprise ultrafiltration and/or diafiltration of the fluid. The recovering can comprise filtering the fluid to remove DNA and/or filtering the fluid to remove virus. The filtering, for removing virus, can comprise passing said fluid through a 0.02 μm filter.

This method can also be used to purify a N-acetylgalactosamine-4-sulfatase or biologically active fragment, analog or mutant thereof.

The purity of rhASB is measured or determined using reverse-phase high performance liquid chromatography ("RP-HPLC"), which separates proteins based on differences in hydrophobicity. This assay uses a C4 column (Phenomenex Jupiter) as the stationary phase and a gradient of water:acetonitrile as the mobile phase. The protein samples are initially injected onto the column in water; under these conditions, all proteins will bind to the column. A gradually increasing concentration of acetonitrile is then infused through the column. This acetonitrile gradient increases the hydrophobicity of the mobile phase, to the point where individual proteins become soluble in the mobile phase and elute from the column. These elution times are accurately reproducible for each individual protein in a mixture. Proteins are detected as peaks on a chromatogram by ultraviolet absorbance at 210 nm. The areas of each peak are calculated, and the sample purity can be calculated as the ratio of the rhASB peak area to the total area of all peaks in the chromatogram. RP-HPLC is a proven high-resolution, reproducible method of determining the purity of rhASB.

Studies prior to this application indicate that the purity of ASB was determined by performing an impurity protein ELISA. This method of using impurity protein ELISA (the details of which are not disclosed) probably used antibodies raised against a mixture of potential host-cell impurity proteins. The ELISA would likely be performed using a standard curve of the same mixture of potential impurity proteins used to generate the antibodies. Test samples would likely be quantitated for impurity levels, relative to this standard mixture. These assays are valuable tools in protein purification, but are less accurate than RP-HPLC for determining the product purity for the following reasons:

(1) In the RP-HPLC assay, the proportions of rhASB and impurities are both determined by the same measurement (UV absorbance). In the ELISA, the impurity concentration is determined by antibody binding whereas the target protein content is determined by another assay method (usually UV absorbance or Bradford). The "percent purity" value should be calculated as the ratio of two quantities with the same units, experimentally determined by the same method.

(2) For the ELISA to work well, the sample detected by the antibody should have the same protein composition as the standard. This is very unlikely to be the case in an impurity protein ELISA. The assay standard for this type of assay would be a mixture of many individual proteins, against which the antibodies were generated. However, only a small subset of impurity proteins should be present in purified rhASB product. Therefore, the antibody reagent will now be detecting a different mixture of proteins, and the response versus the standard will probably be quite nonlinear. When this occurs, the assay yields a different net value for each sample dilution, so one does not know which dilution (if any) is giving the correct value.

(3) In addition, not all potential impurity proteins are immunogenic or immunogenic to the same degree in animals such as rabbits, used to generate the antibodies. Therefore, the impurity level determined by ELISA may only reflect a subset of the impurities present in the purified products. It is entirely possible to have one or more major impurities in the product that are totally undetectable. In contrast, RP-HPLC detects all proteins because UV absorbance is a universal property of protein molecules.

(4) Finally, there are two types of impurities in a purified drug product: product-unrelated impurities (host cell proteins as discussed above) and product-related impurities (degradation products including processed forms and aggregates). The latter cannot be detected by the impurity ELISA but can be readily detected by RP-HPLC.

Therefore, actual numbers obtained from the impurity protein ELISA are open to question, and RP-HPLC numbers are based on a firmer foundation.

An embodiment of this method of purification is depicted in Table 4.

TABLE 4

Method of Purification

| Step | Process |
| --- | --- |
| Harvest Filtration | Filtration through Clarification filters, 0.45 μm filters and finally 0.2 μm filter. Filtered polled harvests are stored in polypropylene bags |
| UF Concentration | Equilibration and flush: 100 mM sodium phosphate, pH 7.3<br>Load: filtered harvest fluid<br>Concentration: Concentration to 20X<br>Filtration: Filter the diluted product through a 0.2 μm filter into storage container |
| pH adjustment and filtration | pH adjustment: Add 10% glacial acetic acid to pooled 20X concentrates to a final pH of equal to or less than about 7.3; preferably, the pH is about 4.0 to 7.3; more preferably, the pH is about 4.5 to 5.5; even more preferably, the pH is about 5.0<br>Load: pooled 20X concentrates<br>Rinse: Water-for Injection (WFI)<br>Filtration through Clarification filters and 0.2 μm filter.<br>Flush: 20 mM sodium acetate, 120 mM sodium chloride, pH 5.0<br>The recovery yield can be at least about 83% |
| Cibracon blue dye interaction chromatography column<br>(Blue Sepharose 6 FF)<br>(Blue, Blue Sepharose) | Pre-Wash: 0.1N sodium hydroxide<br>Wash: Water-for-Injection (WFI)<br>Equilibration: 10 mM sodium phosphate, pH is less than about 6.5; preferably, pH is about 5.0 to 6.5; more preferably, pH is about 6.45<br>Load: pH adjusted and filtered pooled 20X concentrates<br>Wash: 10 mM sodium phosphate, pH 6.45<br>Elution: 10 mM sodium phosphate, 125 mM sodium chloride, pH 6.45<br>Regeneration: 10 mM sodium phosphate, 1.0 M sodium chloride, pH 6.45<br>Sanitization: 0.1 N sodium hydroxide<br>Wash 1: Water-for-Injection (WFI)<br>Wash 2: 10 mM sodium phosphate, 1.0 M sodium chloride, pH 6.45<br>Storage: 20% Ethanol<br>The recovery yield can be at least about 84% |
| Copper chelation chromatography column<br>(Chelating Sepharose FF)<br>(Copper, CC, Copper-Chelating) | Pre-Wash: 0.1N sodium hydroxide<br>Wash: Water-for-Injection (WFI)<br>Charge Buffer: 0.1M cupric sulfate<br>Equilibration: 20 mM sodium acetate, 0.5 M sodium chloride, 10% glycerol, pH is less than about 6.0; preferably, pH is about 3.6 to 5.5; more preferably, pH is about 5.5<br>Load: Adjust glycerol content of pooled Blue Eluates to 10%, by adding 100 mM sodium acetate, 2.0M sodium chloride, 50% glycerol, pH 5.2<br>Wash 1: 20 mM sodium acetate, 0.5 M sodium chloride, 10% glycerol, pH 5.5<br>Wash 2: 20 mM sodium acetate, 0.5 M sodium chloride, 10% glycerol, pH 3.9<br>Elution: 20 mM sodium acetate, 0.5 M sodium chloride, 10% glycerol, pH 3.6<br>Eluate hold for 30–120 minutes prior to adjustment to pH 4.5 with 0.5M NaOH<br>Regeneration: 50 mM EDTA, 1.0M sodium chloride, pH 8.0<br>Sanitization: 0.5M sodium hydroxide<br>Storage: 0.1M sodium hydroxide<br>The recovery yield can be at least about 86% |
| Phenyl hydrophobic interaction chromatography column<br>(Phenyl Sepharose 6 FF High Sub)<br>(Phenyl, Phenyl High Sub) | Pre-Wash: 0.1 N sodium hydroxide<br>Wash: Water-for-Injection (WFI)<br>Equilibration: 20 mM sodium acetate, 2.0 M sodium chloride, pH is about 4.5 to 7.1; preferably, pH is about 4.5<br>Load: Adjust sodium chloride content of Copper Eluate to 2 M, by adding 20 mM sodium acetate, 5 M sodium chloride, pH 4.5<br>Wash 1: 10 mM sodium phosphate, 2.0 M sodium chloride, pH 7.1<br>Wash 2: 20 mM sodium acetate, 2.0M sodium chloride, pH 4.5<br>Elution: 20 mM sodium acetate, 250 mM sodium chloride, pH 4.5<br>Regeneration: 20 mM sodium acetate, pH 4.5<br>Sanitization: 0.5 N sodium hydroxide<br>Storage: 0.1 N sodium hydroxide<br>The recovery yield can be at least about 88% |
| UF/DF, DNA Filtration, Viral Filtration, | Equilibration: 10 mM sodium phosphate, 150 mM sodium chloride, pH 5.8<br>Concentration: Concentration to NMT 1.5 mg/mL<br>Diafiltration: 10 mM sodium phosphate, 150 mM sodium chloride, pH 5.8 |

TABLE 4-continued

Method of Purification

| Step | Process |
| --- | --- |
| Formulation | DNA Filtration: Product filtered through a DNA filter<br>Viral Filtration/Dilution: Product filtered through a 0.02 µm filter and diluted to 1.0 mg/ml<br>Formulation: Polysorbate 80 at a concentration of 50 µg/mL is added<br>Filtration: Filter the diluted product through a 0.2 µm filter into storage container |

The components of the drug product thus obtained are set forth in Table 5. The components of the drug product composition within the scope of the present invention are set forth in Table 6.

TABLE 5

Drug Product Component

| Component | Description |
| --- | --- |
| Active Ingredient | Recombinant human N-acetylgalactosamine-4-sulfatase |
| Excipients | Sodium Phosphate, Monobasic, 1 $H_2O$<br>Sodium Phosphate, Dibasic, 7 $H_2O$<br>Sodium Chloride |
| Container | Kimble Glass, Type I 5 ml clear glass vial, Borosilitcate<br>West pharmaceuticals, S-127 4432150 Grey stopper |

TABLE 6

Drug Product Composition

| Component | Amount |
| --- | --- |
| RhASB | 1 mg/mL |
| Sodium Phosphate, Monobasic, 1 $H_2O$ | 9 mM |
| Sodium Phosphate, Dibasic, 7 $H_2O$ | 1 mM |
| Sodium Chloride | 150 mM |

The invention having been described, the following-examples are offered to illustrate the subject invention by way of illustration, not by way of limitation.

EXAMPLE 1

Clinical Evaluation with Recombinant Human N-acetylgalactosamine-4-sulfatase

Summary

The indication for recombinant human N-acetylgalactosamine-4-sulfatase (rhASB) is the treatment of MPS VI, also known as Maroteaux-Lamy Syndrome. We propose a clinical development program for rhASB consisting of an initial open-label clinical trial that will provide an assessment of weekly infusions of the enzyme for safety, pharmacokinetics, and initial response of both surrogate and defined clinical endpoints. The trial will be conducted for a minimum of three months to collect sufficient safety information for 5 evaluable patients. At this time, should the initial dose of 1 mg/kg not produce a reasonable reduction in excess urinary glycosaminoglycans or produce a significant direct clinical benefit, the dose will be doubled and maintained for an additional three months to establish safety and to evaluate further efficacy.

Objectives

Our primary objective is to demonstrate safety of a weekly infusion of rbASB in patients with MPS VI for a minimum of a three-month period. Measurements of safety will include adverse events, immune response and allergic reactions (complement activation, antibody formation to recombinant enzyme), complete clinical chemistry panel (kidney and liver function), urinalysis, and CBC with differential.

One secondary objective is to evaluate efficacy by monitoring changes in several parameters known to be affected in MPS VI. These include a six-minute walk test (as a measure of exercise tolerance), full pulmonary function (PFT) evaluation, reduction in levels of urinary glycosaminoglycans and hepatomegaly (as measures of kidney and liver GAG storage), growth velocity, joint range of motion, Children's Health Assessment Questionnaire (CHAQ), visual acuity, cardiac function, sleeping studies, and two different global assessments; one performed by the investigator, one performed by the patient/caregiver. A second secondary objective is to determine pharmacokinetic parameters of infused drug in the circulation, and general distribution and half-life of intracellular enzyme using leukocytes and buccal tissue as sources of tissue. It is anticipated that these measures will help relate dose to clinical response based on the levels of enzyme delivered to the lysosomes of cells.

Methods

We will conduct a single center, open-labeled study to demonstrate safety and to evaluate clinical parameters of treatment with rhASB in patients with MPS VI. Patients will be admitted for a two week baseline evaluation that will include a medical history and physical exam, psychological testing, endurance testing (treadmill), a standard set of clinical laboratory tests (CBC, Panel 20, CH50, UA), a MRI or CAT scan of the body (liver and spleen volumetric determination, bone and bone marrow evaluation, and lymph node and tonsillar size), a cardiology evaluation (echocardiogram, EKG, CXR), an airway evaluation (pulmonary function tests), a sleep study to evaluate for obstructive events during sleep, a joint restriction analysis (range of motion will be measured at the elbows and interphalangeal joints), a LP with CNS pressure, and biochemical studies (buccal N-acetylgalactosamine-4-sulfatase activity on two occasions, leukocyte N-acetylgalactosamine-4-sulfatase activity on two occasions, urinary GAG on three occasions, serum generation for ELISA of anti-rhASB antibodies and 24 hour urine for creatinine clearance). In addition to the above evaluations, each patient will be photographed and videotaped performing some physical movements such as attempting to raise their hands over their heads and walking. Patients will be titrated with antihistamines such that pretreatment with these agents could be effectively employed prior to infusion of enzyme. The proposed human dose of 1 mg/kg (50 U/kg) will be administered weekly by i.v. infusion over 4 hours. The patient will remain in the hospital for the first two weeks, followed by short stays for the next four weeks. Treatment for the final six weeks will be conducted at a facility close to the patient's home. Patients will return to the hospital for a complete evaluation at three months. Should dose escalation to 2 mg/kg be required, the patients will follow the same schedule outlined above for the first twelve weeks. Under either scenario, a complete evaluation will also occur at 6 months from the time of entering the trial. Safety will be monitored throughout the trial. Patients completing the trial will be continued on therapy following an extended protocol for as long as safety and efficacy conditions warrant it until BLA approval.

Patient Number and Enrollment Rate

A single patient will be enrolled at the onset of the trial, with two additional patients one month later, and two more patients two weeks later barring any unforeseen complications related to treatment. Additional patients will be admitted should any of the enrolled patients become critically ill, or if a child is in need of an acute clinical procedure for life threatening or harmful conditions.

Diagnosis and Inclusion/Exclusion Criteria

The patient may be male or female, aged five years or older with a documented diagnosis of MPS VI confirmed by measurable clinical signs and symptoms of MPS VI, and supported by a diminished fibroblast or leukocyte ASB enzyme activity level. Female patients of childbearing potential must have a negative pregnancy test (urine β-hCG) just prior to each dosing and must be advised to use a medically accepted method of contraception throughout the study. A patient will be excluded from this study if the patient has previously undergone bone marrow transplantation; is pregnant or lactating; has received an investigational drug within 30 days prior to study enrollment; or has a medical condition, serious intercurrent illness, or other extenuating circumstance that may significantly decrease study compliance.

Dose, Route and Regimen

Patients will receive rhASB at a dose of 1 mg/kg (~50 U/kg) for the first 3 months of the study. In the event that excess urine GAGs are not decreased by a reasonable amount and no clinical benefit is observed, the dose will be doubled. Dose escalation will occur only after all 5 patients have undergone 3 months of therapy. This rhASB dosage form will be administered intravenously over approximately a four-hour period once weekly for a minimum of 12 consecutive weeks. A peripheral intravenous catheter will be placed in the cephalic or other appropriate vein and an infusion of saline begun at 30 cc/hr. The patient will be premedicated with up to 1.25 mg/kg of diphenylhydramine i.v. based on titration experiments completed prior to the trial. rhASB will be diluted into 100 cc of normal saline supplemented with 1 mg/ml human albumin. The diluted enzyme will be infused at 1 mg/kg (about 50 units per kg) over a 4 hour period with cardiorespiratory and pulse oximeter monitoring. The patients will be monitored clinically as well as for any adverse reaction to the infusion. If any unusual symptoms are observed, including but not limited to malaise, shortness of breath, hypoxemia, hypotension, tachycardia, nausea, chills, fever, and abdominal pain, the infusion will be stopped immediately. Based on clinical symptoms and signs, an additional dose of diphenylhydramine, oxygen by mask, a bolus of i.v. fluids or other appropriate clinical interventions such as steroid treatment may be administered. If an acute reaction does occur, an assessment for the consumption of complement in the serum will be tested. A second i.v. site will be used for the sampling required for pharmacokinetic analysis.

Evaluable Patients

The data from any given patient will be considered evaluable as long as no more than two non-sequential infusions are missed during the 12 weeks of therapy. The initial, midpoint and final evaluations must be completed.

Safety

The enzyme therapy will be determined to be safe if no significant acute reactions occur that cannot be prevented by altering the rate of administration of the enzyme, or acute antihistamine or steroid use. The longer-term administration of the enzyme will be determined to be safe if no significant abnormalities are observed in the clinical examinations, clinical labs, or other appropriate studies. The presence of antibodies or complement activation will not by themselves be considered unsafe, but such antibodies will require monitoring by ELISA, and by clinical assessments of possible immune complex disease.

Efficacy

One purpose of this study is to evaluate potential endpoints for the design of a pivotal trial. Improvements in the surrogate and clinical endpoints are expected as a result of delivery of enzyme and removal of glycosaminoglycan storage from the body. Dose escalation will be performed if mean excess urinary glycosaminoglycan levels are not reduced by a reasonable amount over three months and no significant clinical benefit is observed at 3 months. Improvements are expected to be comparable to those observed in the recently completed MPS I clinical trial and should include improved airway index or resolution of sleep apnea, improved joint mobility, and increased endurance.

Although the invention has been described with reference to the presently preferred embodiments, it should be understood that various modifications can be made without departing-from the spirit of the invention. Accordingly, the invention is limited only by the following claims.

EXAMPLE 2

A comprehensive review of the available information for the MPS VI cat and relevant pharmacology and toxicology studies is presented below: Enzyme replacement therapy has been established as a promising treatment for a variety of inherited metabolic disorders such as Gaucher Disease, Fabry Disease and Mucopolysaccharidosis I. In some of these disorders a natural animal model offers the ability to predict the clinical efficacy of human treatment during pre-clinical studies. This was found to be true in MPS I (canine model). With this in mind, studies have been performed with the MPS VI cat prior to the commencement of human studies for this disease. Sufficient safety and efficacy data exist to proceed with a clinical trial in human MPS VI patients.

Studies of rhASB MPS VI cats indicate that no cat has died as a result of drug administration. As predicted, experiments in MPS VI cats also indicate that rhASB uptake is dependent on the presence of mannose 6-phosphate modified carbohydrate sidechains. RhASB in MPS VI cats has also been shown to clear storage from a variety of major organs and moderately alters bone density. Long-term dose-ranging efficacy studies suggest that a dose of 1 mg/kg/week is the lowest concentration to see significant clinical benefits. Studies has also been performed to compare enzyme distribution, clearance of tissue glycosaminoglycan storage, and decrease of urinary glycosaminoglycan levels after bolus and slow (2 hour) infusion. Studies in progress continue to evaluate the safety of weekly infusions of the projected clinical dose of 1 mg/kg of rhASB in cats suffering from MPS VI.

A spontaneous form of MPS VI in several families of Siamese cats was identified in the 1970's (Jezyk, *Science* 198:834–36 (1977)), and detailed reports of the pathological changes in these animals have been published (Haskins, et al., *Am. J. Pathol.* 101:657–674 (1980); Haskins, et al., *J. Am. Vet. Med. Assoc.* 182:983–985 (1983); Konde, et al., *Vet. Radiol.* 28:223–228 (1987)). Although the clinical presentation of these cats is somewhat variable, they all exhibit general changes that have been reported in the literature (Jezyk, et al., *Science* 198:834–36 (1977); Konde, et al., *Vet. Radiol.* 28:223–228 (1987); Crawley, "Enzyme replacement therapy in a feline model of mucopolysaccharidosis type VI" PhD thesis, University of Adelaide, Adelaide, S. Australia, (1998)). Table 6 has been constructed from these sources to provide the "average" changes one would expect to observe in an untreated MPS VI cat:

decreased levels. MPS VI cats urinary glycosaminoglycans remain elevated or continue to increase until reaching steady state after approximately 5 months.

Variability in clinical presentation is seen in affected littermates. In addition to some variability in the timing of onset of particular abnormalities, the time course of progression for some of the clinical and pathological changes is also variable. In general, the bone lesions are typically progressive (Konde et al., *Vet. Radiol.* 28:223–228 (1987)), while the corneal clouding is not. In addition, some paralyzed cats have been noted to improve to severe paresis with time. Studies detailing disease progression in individual cats are limited to clinical (or radiographic) observations. Some of these have distinct pathological correlations, such as neurological deficit and cord compression secondary to proliferation of bony tissue in the thoracolumbar region (Haskins, et al., *J. Am. Vet. Med. Assoc.* 182:983–985 (1983)).

A six-month efficacy study enzyme replacement therapy using recombinant feline ASB in newborn MPS VI cats was conducted. This was prompted by the observation that several treated MPS VI cats developed antibodies to the human enzyme (refer to section 6.5). These antibodies may alter uptake and stability of the enzyme (Brooks, et al.,

TABLE 7

MPS VI Cat Model

| Clinical Observation | Timing of Onset | Changes Relative to Human disease (independent of time) |
|---|---|---|
| Facial dysmorphia: Small head, Broad maxilla, Small ears | 2 months | Similar to human disease |
| Diffuse corneal clouding | 2 months | Similar to human disease |
| Bone abnormalities: Epiphyseal dysplasia, Subluxations, Pectus excavatum | First signs at 2 months - progressive | Similar to human disease - alterations in enchondral calcification |
| Reduced body weight | 3 months | Similar to human disease |
| Reduced cervical spine flexibility | Normal cat value is 180° at all ages. In MPS VI: 3 months: 130–170° 5 months: 45–130° 6 months: 30–100° 11 months: 20–80° | Similar to human disease |
| Osteoporosis/Degenerative Joint Disease | 1 year or more | Similar to human disease |
| Hind limb gait defects Hind limb paresis or paralysis (thoracolumbar cord compressions) | See table below | Carpal tunnel syndrome $C_1$–$C_2$ subluxation, Cervical cord compression secondary to thickened dura more typical |
| Grossly normal liver and spleen | | Liver and spleen enlarged in humans |
| Thickened cardiac valves | | Similar to human disease |
| No CNS lesions - mild lateral ventricle enlargement | | May be comparable to hydrocephalus in human disease |

Other biochemical/morphological determinations indicate that by 35 days, organs of untreated cats have maximal storage of glycosaminoglycans in tissues (Crawley, et al., *J. Clin. Invest.* 99:651–662 (1997)). Urinary glycosaminoglycan levels are elevated at birth in both normal and MPS VI cats but after approximately 40 days, normal cats have

*Biochim. Biophys. Acta* 1361:203–216 (1997)). Feline enzyme was infused at 1 mg/kg weekly. The major conclusions of the study were that urinary GAG, body weight/growth, bone morphometry and clearance of stored material from several tissues was improved relative to the same dose of human recombinant enzyme used in the previous study, that antibodies were not detected beyond the range observed in normal cats, and that the feline enzyme dose at 1 mg/kg was comparable in reversing disease as the human enzyme dose at 5 mg/kg in a head-to-head comparison (Bielicki, et al., *J. Biol. Chem.*, 274:36335–43 (1999)). These studies indicate that an incremental improvement in endpoints and immunogenicity is possible when the cat-derived enzyme is given to cats. This provides additional support to dosing human patients with the human enzyme at 1 mg/kg/week. The results of this study are set forth in Table 7.

TABLE 8

Efficacy of Weekly Bolus Injections of CHO-derived Recombinant Feline ASB in Newborn MPS VI Cats

| Dose | Results 1 mg/kg | |
|---|---|---|
| Duration | 6 months (n = 2) | 3 months (n = 3) |
| Urinary GAGS | Decreased to 2x normal | Decreased to 2x normal |
| Antibody titers | Within range observed in normal cats | To be completed |
| Clinical | | |
| Appearance | Persistent corneal clouding Some resolution of facial dysmorphia Improved body shape | Persistent corneal clouding Some resolution of facial dysmorphia; Improved body shape |
| Weight | Heavier than normal | Slightly lighter than normal |
| Spine Flexibility (normal = 180°) | 160°–180° | Not examined |
| Neurological Radiology | Normal Improved quality Density and dimensions of bone (similar to 1 mg/kg rh4S in ref. 10) | Normal Not examined |
| Gross | | |
| Bone/Cartilage Thickness | Variable; decreased cartilage thickness more uniform subchondral bone (similar to 1 mg/kg rh4S$^a$) | Not examined |
| Spinal Cord Cellular Level | No compressions present | Not examined |
| Liver (Kupffer) | Complete lysosomal storage clearing | Complete lysosomal storage clearing |
| Skin | Almost complete reduction is storage | Mild reduction |
| Cornea/Cartilage (ear, articular) | No clearance of lysosomal storage compared with untreated MPS VI controls | No clearance of lysosomal storage |
| Heart Valves | Significant reduction in lysosomal storage | To be completed |
| Aorta | Almost complete reduction in lysosomal storage | Mild reduction in lysosomal storage |

Table 9 provides a summary of all studies performed using recombinant human ASB in the MPS VI cat model.

TABLE 9

RhASB Study Results

| No. Cat | Dose | Duration (Mo.) | Route of Administration | Urinary GAGS | Histopathology |
|---|---|---|---|---|---|
| 1 | 0/8 mg/kg/14 d 1.5 mg/kg/7 d | 7–22 22–27 | Bolus i.v. Bolus i.v. | Decreased 50% compared to untreated cat | Normalization of vacuolization in liver Significant reduction in kidney and skin |
| 1 | 0.5 mg/kg/14 d 1.4 mg/kg/7 d | 12–23 23–27 | Bolus i.v. Bolus i.v. | Decreased to near normal | No correction in cornea and chondrocytes No kidney immune complex deposition |
| 1 | 0.8 mb/kg/14 d | 2–15 | Bolus i.v. | | |
| 1 | 0.2 mg/kg/8 d | 6 | Bolus i.v. | Marginal reduction compared to untreated | N/A |
| 4 | 1 mg/kg/7 d | 5/6 | Bolus iv. | Decreased and maintained at 3x normal compared to untreated at 10x normal | Complete lysosomal storage clearing in liver cells No evidence or renal impairment or glomerular immune complex deposition Significant reduction of lysosomal storage in heart valves Gradient storage content from media to adventia in aorta |
| 1 | | 11 | Bolus i.v. | | Mild reduction of lysosomal storage of skin (hip joint, dura, kidney No evidence of renal impairment or glomerular deposition No significant changes in lysosomal storage of cornea/cartilage |
| 2 | 5 mg/kg/7 d | 5/6 | Bolus i.v. | Decreased and maintained at 2x normal compared to untreated at 10x normal | Complete lysosomal storage in clearing in liver and skin (hip joint, dura,kidney No evidence of renal impairment or glomerular deposition Near complete reduction in lysosomal storage in heart valves Thin band of vacuolated cells in outer tuncia media |
| 1 | | 11 | Bolus i.v. | | No evidence of renal impairment or glomerular deposition Near complete reduction of lysosomal storage in heart valves Thin band of vacuolated cells in outer tuncia media |
| 2 | 0.5 mg/kg 2x weekly | 6 | Bolus i.v. | Decreased to 3x normal | Complete lysosomal clearing in liver Mild to moderate reduction in skin Variable reduction of lysosomal storage of heart valves Mild reduction of lysosomal storage in aorta |
| 2 | 1 mg/kg/7 d | 1 | Long infusion (2 hr) | Reduced after first or second infusion to | Reduction of lysosomal storage in reticuloendothelial cells and very mild in heat valve and aorta after 5 infusion |

TABLE 9-continued

RhASB Study Results

| No. | Cat Dose | Duration (Mo.) | Route of Administration | Urinary GAGS | Histopathology |
|---|---|---|---|---|---|
| 2 | | | Short infusion (10 min) | below untreated MPS VI cats | |
| 5 | 1 mg/kg/7 d | 6 | Long infusion (2 hr) | | |

EXAMPLE 3

Distribution and Feasibility

An initial study was performed to document enzyme uptake and distribution, and to serve as a pilot study of potential endpoints for future efficacy studies (Crawley, et al., *J. Clin. Invest.* 97:1864–1873 (1996)). Recombinant human ASB was administered by bolus injection to affected cats once per week or once every two weeks at 0.5 up to 1.5 mg/kg. Evaluation of one untreated MPS VI cat (Cat D), and one normal cat provided the values from which comparisons were drawn. The data from the one untreated cat was further supported by historical assessment of 38 additional untreated cats. The acute uptake and distribution studies were conducted in normal cats using an immune assay technique that allowed the detection of human ASB in the presence of normal cat enzyme.

The major conclusions of these studies demonstrated wide uptake of enzyme with the expected predominance of liver and spleen uptake as observed in other enzyme replacement studies in MPS animal models. The uptake efficiency was dependent on the presence of mannose 6-phosphate modified carbohydrate side-chains on the enzyme. The half-life of the enzyme was determined to be 2–4 days. Therapeutically, the enzyme did clear storage from a variety of major organs and did moderately alter bone density. The cornea, bone morphology and cartilage defects were not effectively treated in older MPS VI cats. The study results are summarized in Table 10.

TABLE 10

Summary: Distribution/Feasibility MPS VI Cat Study

| Parameter | Findings | | |
|---|---|---|---|
| Cat | A | B | C |
| Dose | Treated MPS VI 0.8 mg/kg 1.5 mg/kg per 14 d per 7 d | Treated MPS VI 0.5 mg/kg 1.4 mg/kg per 14 d per 7 d | Treated MPS VI 0.8 mg/kg per 14 d |
| Age at dose (mo.) | 7*–22  22–27 | 12*–33  23–27 | 2*–15 |
| Infusion Parameters | 2–10 ml (PBS) via cephalic v. for 5–20 minutes | | |
| Plasma $t_{1/2}$ (i.v. bolus) | 13.7 ± 3.2 min @ 1 mg/kg | | |
| | 45 min @ 7.5 mg/kg | | |
| | All values relative to endogenous feline ASB enzyme four hours after infusion of 1 mg/kg rhASB in normal cats | | |
| | Liver: 495x | | |
| | Spleen: 6x | | |
| | Lung: 22.3x | | |
| | Heart: 4.3x | | |
| | Aorta: 4x | | |
| | Skin: 31x | | |
| | Cartilage: 0x | | |
| | Cornea: 0x | | |
| Tissue $t_{1/2}$ | 2–4 days @ 1 mg/kg in most organs (detectable enzyme in most tissues of cat B, but only in liver of A after 7 days) | | |
| Neurological | Ambulation fluctuated, but improved on higher dose | N/A | Marginal progression to paretic gate by end of study |
| Corneal Opacity | Did not change with therapy (slit lamp exam 3x late in rx) | | |
| Skeletal (x-rays) 4 views every 3 mo. | Lesions progressed (no radiographic improvement Increased bone volume/trabecular # in cat C (received earlier rx) Vertebral compression in cat C | | |
| Anaphylaxis | No anaphylaxis, minimal distress on infusion; | | |
| Antibody response (Ig titers) Untreated MPS VI = 4,000–32,000 | 1 × 10⁶ (plasma could inhibit enzyme activity in vitro) | 64,000 | 64,000 |
| Urinary GAGS (at ~400 days) | Decreased 50% compared to untreated cat | Decreased to near normal | |
| Urinary dermatan sulfate (~400 days) | Midway for all 3 cats (relative to untreated control D and normal) | | |

TABLE 10-continued

Summary: Distribution/Feasibility MPS VI Cat Study

| Parameter | Findings | | |
|---|---|---|---|
| Cat | A | B | C |
| Body Weight | 2.5–3.0 kg vs. normal 4–7 kg | | |
| Liver/Spleen | Grossly normal | | |
| Heart Valves | Grossly normal | | |
| Cartilage | Abnormal thickness and formation | | |
| Microscopy (vacuolization) | Normalization of vacuolization in liver, Significant reduction in kidney and skin, No correction in cornea and chondrocytes | | |
| Kidney immune complex deposition | Absent | | |

EXAMPLE 4

Efficacy in MPS VI Cats Treated from Birth

A long term dose-ranging efficacy study was performed in MPS VI cats starting at birth (Crawley, et al., *J. Clin. Invest.* 99:651–662 (1997)), and is summarized in Table 10. MPS VI cats were treated weekly with bolus i.v. injections of 0.2, 1 and 5 mg/kg of rhASB beginning at birth. A total of 9 cats were treated for 5, 6 or 11 months. In addition, 12 MPS VI and 9 normal cats were included as untreated controls. The major conclusions are that 0.2 mg/kg dose did not alter disease progression in the one cat studied, and the only documented clinical benefit was a reduction in the storage in liver Kupffer cells. Urinary GAG levels decreased to near normal during the trial in the higher dose groups. In addition to improvements in the major organs, the higher doses of therapy from birth were able to prevent or ameliorate the bony deformity of the spine and the abnormal form of many bones. There was a dose-dependent effect on improvement in L-5 vertebral bone mineral volume, bone trabecular thickness, and bone surface density between the 1 and 5 mg/kg doses, although both were equivalent in improving bone formation rate at 5 to 6 months of ERT (Byers, et al., *Bone* 21:425–431 (1997)). The mitral valve and aorta was dependent on dose and was less complete at 1 mg/kg but nearly complete at 5 mg/kg. No improvement of storage in cartilage and cornea was observed at any dose. The study suggests that the 1 mg/kg/week dose is the lowest concentration to see significant clinical benefit. The study results are summarized in Table 11.

TABLE 11

Efficacy of Weekly Bolus Injections of CHO-derived Recombinant Human ASB in Newborn MPS VI Cats (Study PC-BM102-002)

| | | Results | | |
|---|---|---|---|---|
| Dose | 1 mg/kg | | 5 mg/kg | |
| Duration | 5/6 mo | 11 mo | 5/6 mo | 11 mo |
| N | 4 | 1 | 2 | 1 |
| Biochemical | | | | |
| Urinary GAGs | Decreased and maintained at 3x normal compared to untreated at 10x normal | | Decreased and maintained at 2x normal compared to untreated at 10x normal | |
| Clinical | | | | |
| Appearance | Variable changes; Persistent corneal clouding by slit lamp | | Variable changes; Persistent corneal clouding by slit lamp | |
| Weight | Intermediate (no rx vs. normal) | | Intermediate (no rx vs. normal) | |
| Spine Flexibility (normal = 180) (untreated MPS VI = 90°) | 130–160° | 90° | 180° | 160° |
| Neurological | 1 of 4 mild hindlimb paralysis | No deficits | No deficits | No deficits |
| Radiology | Improved bone quality, density and dimensions | | Improved bone quality, density and dimensions Possibly superior to 1 mg/kg | |
| Gross | | | | |
| Bone/Cartilage Thickness | Variability, but improved | Degenerative joint disease present | Variability, but improved | Degenerative joint disease present |

TABLE 11-continued

Efficacy of Weekly Bolus Injections of CHO-derived Recombinant Human ASB in Newborn MPS VI Cats (Study PC-BM102-002)

| Dose | 1 mg/kg | | 5 mg/kg | |
|---|---|---|---|---|
| | | | Results | |
| Duration | 5/6 mo | 11 mo | 5/6 mo | 11 mo |
| N | 4 | 1 | 2 | 1 |
| Spinal Cord | 1 of 4 with several mild compressions | No compressions | No cord compressions | |
| Cellular Level | | | | |
| Liver (Kupffer) | Complete lysosomal storage clearing | Maintained | Complete lysosomal storage clearing | Maintained |
| Skin (hip Joint, Dura, Kidney) | No evidence of renal impairment or glomerular immune complex deposition | Mild reduction in lysosomal storage No evidence of renal impairment or glomerular deposition | Complete lysosomal storage clearing No evidence of renal impairment or glomerular deposition | Maintained No evidence of renal impairment or glomerular deposition |
| Cornea/Cartilage (ear, articular) | NA | No significant changes in lysosomal storage | NA | No significant changes in lysosomal storage |
| Heart Valves | Significant (Variable) reduction in lysosomal storage | Significant (variable) reduction in lysosomal storage near complete | Near complete reduction in lysosomal storage | |
| Aorta | Gradient of storage content from media to adventitia | | Thin band of vacuolated cells in outer tunica media | |

EXAMPLE 5

Efficacy of Twice Weekly Infusions of Recombinant Human ASB in Newborn MPS VI Cats A six-month study was performed in newborn cats to evaluate a 0.5 mg/kg infusion given twice weekly. In addition, the enzyme used in this study was derived exclusively from the CSL-4S-342 cell line. The major conclusions of the study include that compared with the previously reported 1 mg/kg weekly dose, this study produced similar improvements in physical, biochemical, neurological and radiographic parameters. The most notable differences were slightly worsened cervical spine flexibility, and less clearance of lysosomal storage in the denser connective tissues such as the heart valves and aorta. The results are summarized in Table 12.

TABLE 12

Efficacy of Twice Weekly Bolus Injections of CHO-derived Recombinant Human ASB in Newborn MPS VI Cats

| Parameter | Results |
|---|---|
| Dose | 0.5 mg/kg |
| Duration | 2x weekly: 6 months (n = 2; cats 225 f, 226 m) |
| Urinary GAGs | Decreased to 3x normal |
| Antibody titres | Within range observed in normal cats |
| Clinical | |
| Appearance | Persistent corneal clouding Some resolution of facial dysmorphia Improved body shape |
| Weight | Intermediate (between no treatment and normal) |
| Spine Flexibility (normal = 180°) | 90°–150° |
| Neurological | No hind limb paralysis |
| Radiology | Improved quality, density and dimensions of bone (similar to 1 mg/kg rh4S in ref. 110 |
| Gross | |
| Bone/Cartilage Thickness | Variable; decreased cartilage thickness and and more uniform subchondral bone (similar to 1 mg/kg rh4S[a]) |
| Spinal Cord Cellular Level | No compressions present |
| Liver (Kupffer) | Complete lysosomal clearing |
| Skin | Mild to moderate reduction in storage |
| Cornea/Cartilage (ear, articular) | No clearance of lysosomal storage compared with untreated MPS VI controls |
| Heart Valves | Variable reduction in lysosomal storage (complete in 225 f; no change from untreated in 226 m) |
| Aorta | Mild reduction in lysosomal storage |

EXAMPLE 6

Evaluation of Enzyme Uptake and Distribution as a Function of the Rate of Enzyme Infusion in MPS VI Cats The primary goal of this study was to compare enzyme distribution, clearance of tissue GAG storage, and decrease of urinary GAG levels after bolus infusion and after slow (2 hour) infusion of an identical 1 mg/kg dose. The slow administration proposal is based on experience from pre-clinical and clinical studies of α-L-iduronidase for the treatment of MPS I. In addition, the study provided the first data that enzyme produced at BioMarin from cell line CSL-4S-342 is biologically active and safe. Major conclusions of the study include that all four cats (two per group) treated in this study showed no acute adverse reaction to either the slow or fast infusion, and no detrimental effects of repeated enzyme infusions. However, bolus infusion results in high liver uptake which is not preferred. Slow infusion provides better distribution into tissues and therefore is a preferred method for clinical trial.

The tissue distribution of rhASB obtained in the study suggested that 2-hour infusions might increase enzyme levels in other organs apart from the liver, including increased activity in the brain. Reduction in urinary GAG was observed immediately after the first or second infusion to levels below the range observed in untreated MPS VI cats. Correction of lysosomal storage was observed in reticuloendothelial cells and very mild in some fibroblasts (heart valve) and smooth muscle cells (aorta) after 5 infusions. No other significant clinical response to infusions was observed in either group, however this was not unexpected due to the short duration of the study, and due to therapy starting after significant disease changes had already developed. The extended 2-hour infusion was safe and well tolerated relative to the shorter protocols used in previous studies. The 2-hour infusion may provide improvement in enzyme distribution based on the one cat that was evaluable for enzyme tissue distribution.

EXAMPLE 7

6 Month Safety Evaluation of Recombinant Human N-acetylgalactosamine-4-sulfatase in MPS VI Affected Cats Two 6 month studies in MPS VI cats have been initiated using the enzyme produced by the manufacturing process according to the present invention. The purpose of these studies is to evaluate the safety and efficacy of weekly infusions of the projected human clinical dose of rhASB in cats suffering from MPS VI. Study 6 involves kittens dosed initially at 3 to 5 months of age. Study 7 involves kittens treated from birth with weekly infusions of the projected human clinical dose of rhASB. The studies are intended to access potential toxicology. Cats will be observed for changes in behavior during infusion of the recombinant enzyme to assess possible immune responses. Serum will be monitored for complement depletion and for the formation of antibody directed against the recombinant enzyme. General organ function will be monitored by complete clinical chemistry panels (kidney and liver function), urinalysis, and complete blood counts (CBC) with differential. Urinary glycosaminoglycan levels will be monitored on a weekly basis at a set time points relative to enzyme infusion. Evidence of clinical improvements in disease will be documented. These data will provide additional assessment of the potential efficacy of the treatment and will validate the activity and uptake of the enzyme in vivo. The studies have and will be conducted in a manner consistent with the principles and practices of GLP regulations as much as possible.

Preliminary results of the first study indicate that administration of rhASB has not had any detrimental effects on any of the animals, with bodyweights and clinical chemistries generally maintained within reference ranges. However, both of the cats with significantly elevated antibody titers developed abnormal clinical signs during infusions, however both animals behaved normally once enzyme infusions ceased and did not appear to suffer any longer tem ill effects. Extended infusion times (4 hours) and increased premedication antihistamines have allowed continued therapy in the cats without any abnormal clinical signs. Mild reduction in urinary GAG levels suggest some efficacy of therapy in reducing stored glycosaminoglycans in tissues or circulation, however fluctuations in these levels were observed over time making interpretation difficult. None of the 5 cats have shown obvious clinical improvements in response to ERT, but this will require at least 6 month treatment based on previous studies[23]. Antibody titers have developed in four out of the five cats, with noticeable increases in titers observed after 2 months of ERT. Two of these cats have developed significantly elevated titers after 2 or 3 months.

EXAMPLE 8

Safety Profile for MPS VI Cats Treated with rhASB

A study has commenced enrolling affected cats that were treated within 24 hours of birth. Forty-one MPS VI cats have been treated using rhASB. Administration of enzyme to normal cats has been restricted to one to two cats to confirm acute safety of new batches prior to exposure of the valuable affected animals to therapy. In summary, no MPS VI cat has died as a result of drug administration, although four cats have died as a result of viral infection or an underlying congenital abnormality. Enzyme for the studies was produced according to the production methods of the present invention. The preliminary data are set forth in Table 13.

TABLE 13

MPS VI Cat Efficacy Study Summary from Hopwood Laboratory

| Study # | # of Cats | Dose/wk (mg/kg) | Rx Length (mos.) | Mortality |
|---|---|---|---|---|
| 1 | 2 | Variable | 13–21 | None |
|   | 1 |  |  |  |
| 2 | 1 | 0.2 | 5 | None |
| 2 | 1 | 0.2 | 1 | Died: congenital heart defect |
| — | 2 | 0.5 | 3–5 | 1 died parvovirus |
| 2 | 4 | 1 | 3–11 | 1 died parvovirus |
|   | 2 |  |  |  |
| — | 1 | 1 | 6 (s.c.) | None |
| — | 4 | 1 | 6 | None |
| 2 | 2 | 5 | 3–11 | 1 died parvovirus |
|   | 2 |  |  |  |
| 4 | 2 | 0.5 (twice) | 5 | None |
| — | 3 | 0.5 (twice) | 5 | None |
| 5 | 4 | 1 | 1 | None |
| 6 | 5 | 1 | Started | None |
| 7 | 5 | 1 | Started | None |

EXAMPLE 9

Method of Manufacture and Purificationm (Perfusion Process)

A process flow diagram comparing the purification processes for the fed batch and perfusion-based cell culture processes is provided in Table 14. Comparisons to the fed batch purification process as well as details of the specific changes implemented for the purification of the perfusion process material are summarized in Table 15. Table 16 depicts the purification method used for the perfusion-based cell cultures.

TABLE 14

Purification Process Comparison between Batch and Perfusion Processes

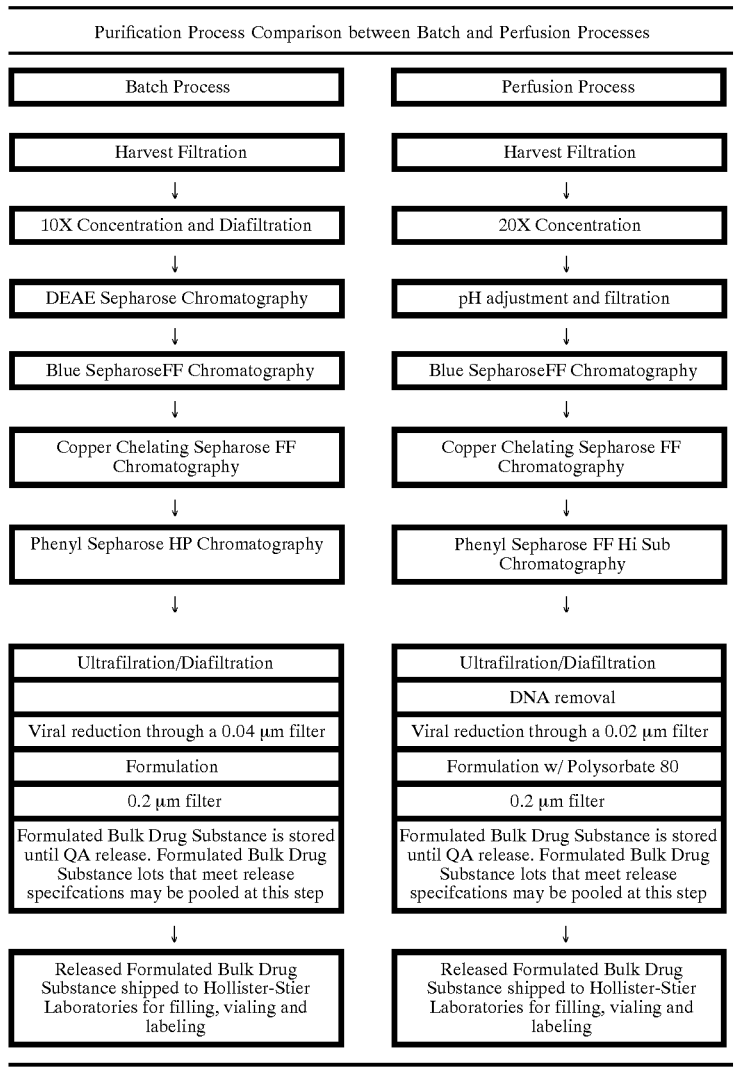

TABLE 15

Summary Description of Purification Changes

| Production Step | Description (Batch) | Description (Perfusion) |
|---|---|---|
| PURIFICATION PROCESS | | |
| Concentration/ Diafiltration | Tangential Flow Filtration: 2.8 m² Albumin retentive MWCO filters Operation: Concentration to 10X Diafiltered against 5 volumes 10 mM sodium phosphate, 100 mM sodium chloride, pH 7.3 | Changes: Tangential Flow Filtration: 5.6 m² Albumin retentive MWCO filters Operation: Concentration to 20X No diafiltration, system rinsed with 100 mM sodium phosphate, pH 7.3 Rationale: Reduction of volume for storage at 4° C. |
| | ↓ | |
| DEAE Sepharose FF Flow-Through Chromatography | Column: 2 × 30 cm diameter × 33 cm height Pre-Wash: 0.1 N sodium hydroxide Wash: Water-for-Injection (WFI) Neutralize: 100 mM sodium phosphate, pH 7.3 Equilibration: 10 mM sodium | Step deleted |

TABLE 15-continued

Summary Description of Purification Changes

| Production Step | Description (Batch) | Description (Perfusion) |
|---|---|---|
| | phosphate, 100 mM sodium chloride, pH 7.3<br>Load: concentrated/diafiltered harvest<br>Wash: 10 mM sodium phosphate, 100 mM sodium chloride, pH 7.3<br>Strip: 10 mM sodium phosphate, 1.5 M sodium chloride, pH 7.3<br>Regeneration: 10% glacial acetic acid<br>Wash: Water-for-Injection (WFI)<br>Sanitization: 0.5 N sodium hydroxide<br>Storage: 0.1 N sodium hydroxide<br>↓ | |
| pH adjustment and filtration | | pH adjustment: addition of 10% glacial acetic acid to pooled 20X concentrates to a final pH 5.0<br>Load: pooled 20X concentrates<br>Filtration through clarification filters and 0.2 µm filter<br>Flush: 20 mM sodium acetate, 120 mM sodium chloride, pH 5.0<br>Rationale:<br>Increases rhASB binding capacity of the subsequent Blue Sepharose resin column. |
| | ↓ | |
| Blue Sepharose FF Chromatography | Column:<br>20 cm diameter × 11 cm height<br>Pre-Wash: 0.1 N sodium hydroxide<br>Wash: Water-for-Injection (WFI)<br>Neutralization: 1 M sodium acetate, pH 5.5<br>Equilibration: 20 mM sodium acetate, 150 mM sodium chloride, pH 5.5<br>Load: DEAE flow through adjusted to 20 mM sodium acetate, 150 mM sodium chloride, pH 5.5<br>Wash: 20 mM sodium acetate, 150 mM sodium chloride, pH 5.5<br>Elution: 20 mM sodium acetate, 500 mM sodium chloride, pH 5.5<br>Regeneration: 20 mM sodium acetate, 1.0 M sodium chloride, pH 5.5<br>Sanitization: 0.1 N sodium hydroxide<br>Wash 1: Water-for-Injection<br>Wash 2: 1 M sodium acetate, pH 5.5<br>Storage: 20% Ethanol<br>↓ | Change:<br>Column:<br>45 cm diameter × 16 cm height<br>Neutralization: omitted<br>Equilibration: 10 mM sodium phosphate, pH 6.45<br>Load: pooled 20X concentrates, pH adjusted to 5.0 and filtered.<br>Wash: 10 mM sodium phosphate, pH 6.45<br>Elution: 10 mM sodium phosphate, 125 mM sodium chloride, pH 6.45<br>Regeneration: 10 mM sodium phosphate, 1.0 M sodium chloride, pH 6.45<br>Wash 2: 10 mM sodium phosphate, 1.0 M sodium chloride, pH 6.45<br>Rationale:<br>Conditions allow improved removal of potential CHO impurities allowing for the deletion of DEAE Sepharose Chromatography. |
| Copper Chelating Sepharose FF Chromatography | Column:<br>14 cm diameter × 9 cm height<br>Pre-Wash: 0.1 N sodium hydroxide<br>Wash: Water-for-Injection (WFI)<br>Charge Buffer: 0.1 M cupric sulfate<br>Equilibration: 20 mM sodium acetate, 0.5 M sodium chloride, 10% glycerol, pH 6.0<br>Load: Adjust glycerol content of Blue Eluate to 10%, by adding 20 mM sodium acetate, 500 mM sodium chloride, 50% glycerol, pH 6.0<br>Wash 1: 20 mM sodium acetate, 0.5 M sodium chloride, 10% glycerol, pH 6.0<br>Wash 2: 20 mM sodium acetate, 0.5 M sodium chloride, 10% glycerol, pH 4.0<br>Wash 3: 20 mM sodium acetate, 0.5 M sodium chloride, 10% glycerol, pH 3.8<br>Elution: 20 mM sodium acetate, 0.5 M sodium chloride, 10% glycerol, pH 3.6<br>Regeneration: 50 mM EDTA, 1.0 M sodium chloride, pH 8.0<br>Sanitization: 0.5 M sodium hydroxide<br>Storage: 0.1 M sodium hydroxide<br>↓ | Changes:<br>Column:<br>40 cm diameter × 16 cm height<br>Equilibration: 20 mM sodium acetate, 0.5 M sodium chloride, 10% glycerol, pH 5.5<br>Load: Adjust glycerol content of pooled Blue Eluate to 10%, by adding 100 mM sodium acetate, 2.0 M sodium chloride, 50% glycerol, pH 5.2<br>Wash 1: 20 mM sodium acetate, 0.5 M sodium chloride, 10% glycerol, pH 5.5<br>Wash 2: 20 mM sodium acetate, 0.5 M sodium chloride, 10% glycerol, pH 3.9<br>Wash 3: omitted<br>Rationale:<br>Consistent and reproducible product purity obtained with modified step |

TABLE 15-continued

Summary Description of Purification Changes

| Production Step | Description (Batch) | Description (Perfusion) |
|---|---|---|
| Viral Inactivation | Pooled Eluate fractions held for 30–120 minutes prior to adjustment to pH 4.5 with 0.5 M NaOH | No Change |
| Phenyl Sepharose Chromatography | Column: 10 cm diameter × 16 cm height Resin: Phenyl Sepharose High Performance Pre-Wash: 0.1 N sodium hydroxide Wash: Water-for-Injection (WFI) Equilibration: 20 mM sodium acetate, 3.0 M sodium chloride, pH 4.5 Load: Adjust sodium chloride content of Copper Eluate to 3 M, by adding 20 mM sodium acetate, 5 M sodium chloride, pH 4.5 Wash 1: 20 mM sodium acetate, 3.0 M sodium chloride, pH 4.5 Wash 2: 20 mM sodium acetate, 1.6 M sodium chloride, pH 4.5 Elution: 20 mM sodium acetate, 1 M sodium chloride, pH 4.5 Regeneration: 20 mM sodium acetate, pH 4.5 Sanitization: 0.5 N sodium hydroxide Storage: 0.1 N sodium hydroxide | Change: Column: 40 cm diameter × 16 cm height Resin: Phenyl Sepharose High Sub Fast Flow Equilibration: 20 mM sodium acetate, 2.0 M sodium chloride, pH 4.5 Load: Adjust sodium chloride content of Copper Eluate to 2 M, by adding 20 mM sodium acetate, 5 M sodium chloride, pH 4.5 Wash 1: 10 mM sodium phosphate, 2.0 M sodium chloride, pH 7.1 Wash 2: 20 mM sodium acetate, 2.0 M sodium chloride, pH 4.5 Elution: 20 mM sodium acetate, 250 mM sodium chloride, pH 4.5 Rationale: Alternate resin has more favorable flow characteristics and capacity for rhASB. Wash 1 allows more robust clearance of potential protein impurities. |
| UF/DF Final | Tangential Flow Filtration: <0.4 $m^2$ MWCO 10 kDa Filters. Equilibration: 10 mM sodium phosphate, 150 mM sodium chloride, pH 5.8 Concentration: Concentration to NMT 1.5 mg/mL Diafiltration: 10 mM sodium phosphate, 150 mM sodium chloride, pH 5.8 | Change: Tangential Flow Filtration: 2.8 $m^2$ MWCO 10 kDa Filters. |
| DNA Removal | Not Done | New Step: DNA Filtration: Product filtered through an ion exchange-based DNA filter. Rationale: Additional DNA clearance to compensate for deletion of DEAE Flow-Through Chromatography step. |
| Formulation | Diluted to 1.0 mg/ml with 10 mM sodium phosphate, 150 mM sodium chloride, pH 5.8 | |
| Viral filtration | Viral Filtration: Product filtered though a 0.04 µm filter | Change: Viral Filtration: Product filtered though a 0.02 µm filter Rationale: Use of smaller pore size to enhance viral clearance. |
| Formulation | Step occurs earlier in process (Prior to viral filtration) | Change: Diluted to 1.0 mg/ml with 10 mM sodium phosphate, 150 mM sodium chloride, pH 5.8 Formulation: Polysorbate 80 is added to a concentration of 50 µg/mL. |
| Filtration | Filtration: Filter the diluted product through a 0.2 µm filter into storage container | No Change |

TABLE 16 rhASB Purification Method (Perfusion Process)

| Step | Process |
| --- | --- |
| Harvest Filtration | Filtration through Clarification filters, 0.45 µm filters and finally 0.2 µm filter. Filtered polled harvests are stored in polypropylene bags |
| UF Concentration | Equilibration and flush: 100 mM sodium phosphate, pH 7.3<br>Load: filtered harvest fluid<br>Concentration: Concentration to 20X<br>Filtration: Filter the diluted product through a 0.2 µm filter into storage container |
| pH adjustment and filtration | pH adjustment: Add 10% glacial acetic acid to pooled 20X concentrates to a final pH of 5.0<br>Load: pooled 20X concentrates<br>Rinse: Water-for Injection (WFI)<br>Filtration through Clarification filters and 0.2 µm filter.<br>Flush: 20 mM sodium acetate, 120 mM sodium chloride, pH 5.0 |
| Blue Sepharose 6 FF (Blue, Blue Sepharose) | Pre-Wash: 0.1 N sodium hydroxide<br>Wash: Water-for-Injection (WFI)<br>Equilibration: 10 mM sodium phosphate, pH 6.45<br>Load: pH adjusted and filtered pooled 20X concentrates<br>Wash: 10 mM sodium phosphate, pH 6.45<br>Elution: 10 mM sodium phosphate, 125 mM sodium chloride, pH 6.45<br>Regeneration: 10 mM sodium phosphate, 1.0 M sodium chloride, pH 6.45<br>Sanitization: 0.1 N sodium hydroxide<br>Wash 1: Water-for-Injection (WFI)<br>Wash 2: 10 mM sodium phosphate, 1.0 M sodium chloride, pH 6.45<br>Storage: 20% Ethanol |
| Chelating Sepharose FF (Copper, CC, Copper-Chelating) | Pre-Wash: 0.1 N sodium hydroxide<br>Wash: Water-for-Injection (WFI)<br>Charge Buffer: 0.1 M cupric sulfate<br>Equilibration: 20 mM sodium acetate, 0.5 M sodium chloride, 10% glycerol, pH 5.5<br>Load: Adjust glycerol content of pooled Blue Eluates to 10%, by adding 100 mM sodium acetate, 2.0 M sodium chloride, 50% glycerol, pH 5.2<br>Wash 1: 20 mM sodium acetate, 0.5 M sodium chloride, 10% glycerol, pH 5.5<br>Wash 2: 20 mM sodium acetate, 0.5 M sodium chloride, 10% glycerol, pH 3.9<br>Elution: 20 mM sodium acetate, 0.5 M sodium chloride, 10% glycerol, pH 3.6<br>Eluate hold for 30–120 minutes prior to adjustment to pH 4.5 with 0.5 M NaOH<br>Regeneration: 50 mM EDTA, 1.0 M sodium chloride, pH 8.0<br>Sanitization: 0.5 M sodium hydroxide<br>Storage: 0.1 M sodium hydroxide |
| Phenyl Sepharose 6 FF High Sub (Phenyl, Phenyl High Sub) | Pre-Wash: 0.1 N sodium hydroxide<br>Wash: Water-for-Injection (WFI)<br>Equilibration: 20 mM sodium acetate, 2.0 M sodium chloride, pH 4.5<br>Load: Adjust sodium chloride content of Copper Eluate to 2 M, by adding 20 mM sodium acetate, 5 M sodium chloride, pH 4.5<br>Wash 1: 10 mM sodium phosphate, 2.0 M sodium chloride, pH 7.1<br>Wash 2: 20 mM sodium acetate, 2.0 M sodium chloride, pH 4.5<br>Elution: 20 mM sodium acetate, 250 mM sodium chloride, pH 4.5<br>Regeneration: 20 mM sodium acetate, pH 4.5<br>Sanitization: 0.5 N sodium hydroxide<br>Storage: 0.1 N sodium hydroxide |
| UF/DF, DNA Filtration, Viral Filtration, Formulation | Equilibration: 10 mM sodium phosphate, 150 mM sodium chloride, pH 5.8<br>Concentration: Concentration to NMT 1.5 mg/mL<br>Diafiltration: 10 mM sodium phosphate, 150 mM sodium chloride, pH 5.8<br>DNA Filtration: Product filtered through a DNA filter<br>Viral Filtration/Dilution: Product filtered through a 0.02 µm filter and diluted to 1.0 mg/ml<br>Formulation: Polysorbate 80 at a concentration of 50 µg/mL is added<br>Filtration: Filter the diluted product through a 0.2 µm filter into storage container |

All purification columns are regenerated prior to use, sanitized after use and stored in the appropriate buffers as indicated in Tables 15 and 16.

Purification Raw Materials

All materials are supplied by qualified vendors.

TABLE 17

Raw Materials for Purification

| Ingredient | Grade |
| --- | --- |
| Glacial Acetic Acid | USP |
| Cupric Sulfate Pentahydrate | USP |
| Edetate Disodium | USP |
| Dehydrated Alcohol, USF (Ethanol, 200 Proof) | USP |
| Glycerine | USP |
| Sodium Acetate, Trihydrate | USP |
| Sodium Chloride | USP |
| Sodium Hydroxide 50% w/w Solution | Reagent Grade |
| Sodium Phosphate, Dibasic, Heptahydrate | USP/EP |
| Sodium Phosphate, Monobasic, Monohydrate | USP |
| Hydrochloric Acid, 6 N Volumetric Solution | Reagent Grade |

TABLE 17-continued

Raw Materials for Purification

| Ingredient | Grade |
|---|---|
| Polysorbate 80, MF/EP (CRILLE 4 HP) | NF/EP |
| Water-for-Injection, Packaged in Bulk | USP |

The glycerine to be utilized is to be derived from a synthetic process. All raw materials used are to be in compliance with the latest version of the CPMP/CVMP Note for Guidance entitled, "Minimising the Risk of Transmitting Animal Spongiform Encephalopathy Agents Via Human and Veterinary Medicinal Products," in which tallow derivatives such as glycerol and fatty acids manufactured by rigorous processes involving high temperatures and pressure conditions or chemical reactions known to be terminally hostile to the bovine spongiform encephalopathic (BSE) agent are thought unlikely to be infectious. Thus, the risk of BSE transmission from the glycerine is considered to be low.

The viral safety of rhASB is confirmed by a combination of selection and qualification of vendors, raw material testing, cell bank characterization studies, viral removal studies and inactivation capacity of the rhASB purification process, and routine lot release testing. Relevant US, EU, and ICH regulations and guidelines have been referenced to ensure the viral safety of rhASB.

Column Chromatography, DNA Removal and Viral Filtration

RhASB is now purified using a series of chromatography and filtration steps. The harvest fluid is concentrated to 20× by ultrafiltration, pH adjusted, filtered and loaded onto a Blue Sepharose Fast Flow chromatography column (45 cm×16 cm). The Blue Sepharose Fast Flow eluate is filtered prior to loading on to a Copper Chelating Sepharose column. The Copper eluate is filtered prior to loading on to a Phenyl Sepharose Fast Flow High Sub column. All three column chromatography purification steps are run in a bind and elute mode. The Phenyl Sepharose column eluate is passed through an anion exchange filter and viral reduction filter prior to concentration and buffer exchange by ultrafiltration.

Viral Removal/Inactivation Studies

Two studies were conducted to assess the viral reduction capacity of the modified rhASB purification process. Studies were performed at BioReliance (Rockville, Md.) using two model virus systems, Xenotropic murine leukemia virus (XMuLV) and Murine Minute Virus (MMV). XMuLV is an enveloped single-stranded RNA retrovirus with low resistance to physico-chemical inactivation. MMV is a small, non-enveloped single-stranded DNA virus with high resistance to physico-chemical agents.

These studies evaluated two chromatographic steps (Copper Chelating Sepharose FF and Phenyl Sepharose FF High Sub) and the viral filter (0.02 μm) used in the rhASB purification process. Spike and recovery studies were performed using scaled down versions of the process steps. The critical parameters maintained were retention times and matrix-solution interactions. This was achieved by replicating the buffers, linear flow rates and column heights but adjusting for column diameter. Materials used in the study (product and buffers) were collected from actual full scale production.

Chromatography columns (Copper Chelating Sepharose and Phenyl Sepharose) were packed and pre-run with either typical rhASB loads (blank) or loads spiked with viral buffer prior to shipping to BioReliance. Chromatograms and product yields in the presence of viral buffers were comparable to blank runs. Identical column loads were spiked with either XMuLV or MMV immediately prior to chromatography. The amount of viral reduction for each of the evaluated steps was determined by comparing the viral burden in the column loads and eluates. A summary of the results for this study are shown in Table 18.

TABLE 18

Reduction Factors for XmuLV and MMV

| Process Step | XMuLV Log Reduction | MMV Log Reduction |
|---|---|---|
| Blue Sepharose | not tested | not tested |
| Copper Chelating (+ low pH hold) | ≥3.51 ± 0.52 | ≥2.71 ± 0.52 |
| Phenyl Sepharose | ≥3.54 ± 0.36 | ≥1.72 ± 0.64 |
| DNA Filtration | not tested | not tested |
| Viral Filtration | ≥5.51 ± 0.43 | ≥4.76 ± 0.00 |
| Total log Reduction | ≥12.56 | ≥9.19 |

In-Process Testing

Figure 3:
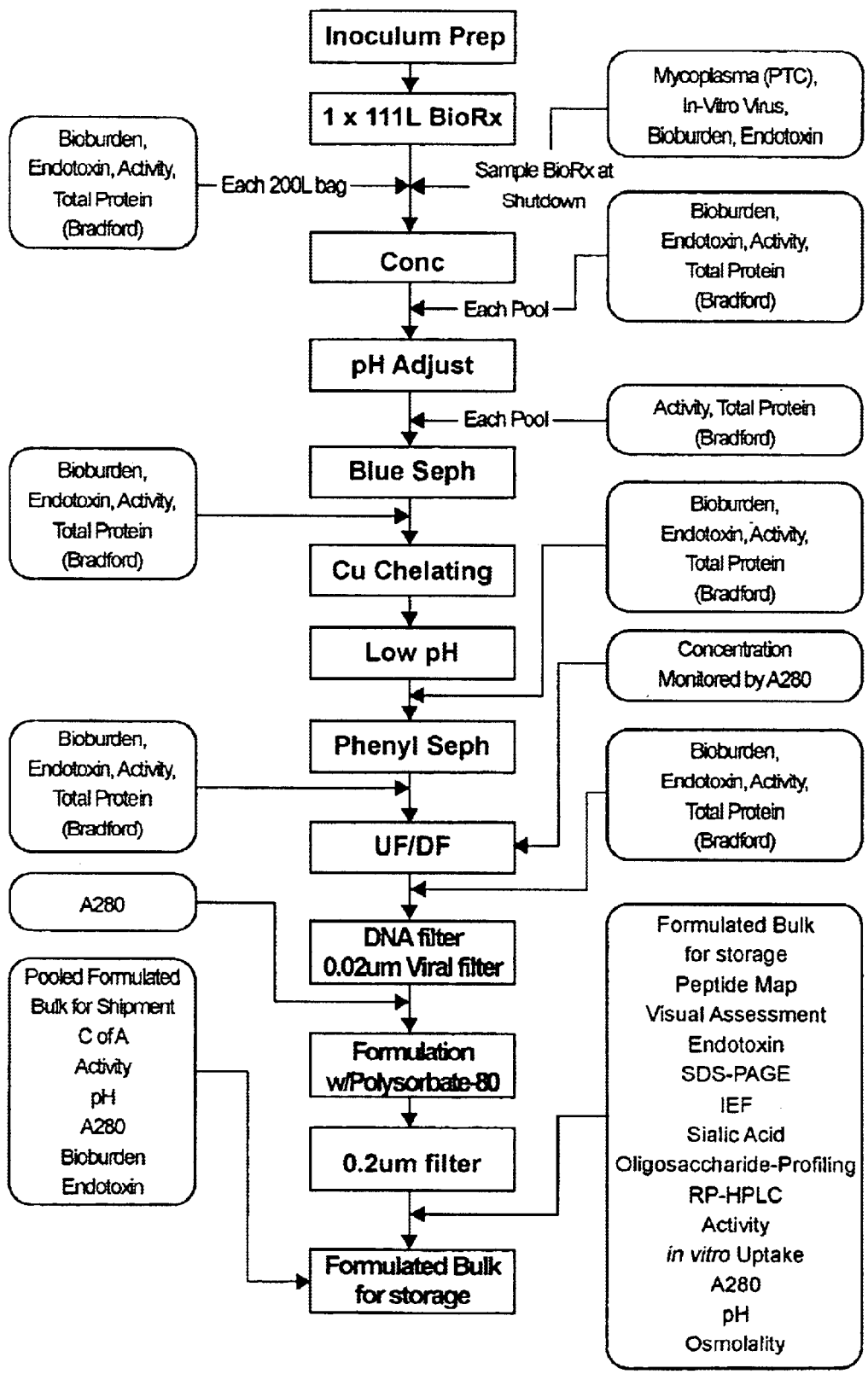
FIG. 3 provides the flow diagram of the method for purifying a human N-acetylgalactosamine-4-sulfatase (ASB) according to the perfusion process method (Tables 14 and 15).

In-process testing is performed throughout the process and is illustrated in FIG. 3. In-process testing of the harvest cell culture fluid and the purification intermediates is described in Tables 19 and 20.

TABLE 19

In-Process Testing of the Harvested Cell Culture Fluid

| Test | Action Levels |
|---|---|
| Bacterial Endotoxin by LAL (USP/EP) | ≥2 EU/mL |
| Bioburden (USP/EP) | ≥1 cfu/10 mL |
| Total Protein by Bradford and Activity | Results used for the calculation of the Blue Sepharose column load |
| Mycoplasma[1] | Negative (Release Specification) |
| In vitro Assay For The Presence of Viral Contaminants[1] | Negative (Release Specification) |

[1]Sampling is performed at multiple time points during the cell culture harvest stage of manufacturing. The last sample removed prior to the termination of the cell culture process is tested and a negative result is required for lot release.

TABLE 20

In-Process Testing of Purification Intermediates

| Test | Action Levels |
|---|---|
| Bacterial Endotoxin by LAL (USP/EP) | ≥3 EU/mL in column eluates[1] |
| Bioburden (USP/EP) | ≥20 cfu/mL pre-filtration[1] |
|  | ≥1 cfu/100 mL in Formulated Bulk Drug Substance (FBDS)[2] |
| Activity | Result used for the calculation of the Copper Chelating and Phenyl Sepharose column loads |
| Total Protein by UV-Vis Spectrophotometry | Result used for the calculation of the protein concentration for the UF/DF |

[1]Results exceeding action levels are investigated per standard operating procedures.
[2]If results exceed action level, the FBDS will be 0.2 μm filtered into appropriate sterile storage containers and then quarantined pending release for shipment to filling sites.

Results of Perfusion Method of Purifying Precursor rhASB

Table 21 provides data on the degree of purity of rhASB obtained using the purification methods described in Tables 15 and 16. The "Purity by RP-HPLC" column indicates the degree of purity obtained for the combined amount of both the precursor and mature forms of rhASB.

TABLE 21 rhASB Lot Release Results

| Lot | Purity by RP-HPLC | Presence of the processed forms* | Manufacturing process |
|---|---|---|---|
| AP60028 | 99.6 | – | Batch process |
| AP60029 | 98.8 | + | Batch process |
| AP60030 | 98.7 | + | Batch process |
| AP60031 | 99.1 | – | Batch process |
| AP60032 | 99.8 | – | Batch process |
| AP60033 | 99.4 | – | Batch process |
| AP60035 | 98.7 | – | Batch process |
| AP60036 | 99.4 | – | Batch process |
| AP60038 | 99.6 | – | Batch process |
| AP60039 | 99.3 | – | Batch process |
| AP60040 | 99.1 | – | Batch process |
| AP60101 | 99.3 | – | Batch process |
| AP60102 | 98.9 | – | Batch process |
| AP60103 | 99.0 | – | Batch process |
| AP60104 | 99.0 | + | Batch process |
| AP60105 | 99.0 | – | Batch process |
| AP60106 | 99.2 | – | Batch process |
| AP60107 | 99.4 | – | Batch process |
| AP60108 | 99.7 | – | Perfusion process |
| AP60109 | 99.8 | – | Perfusion process |
| AP60201 | 99.0 | N/A | Perfusion process |
| AP60202 | 100 | – | Perfusion process |

*"+" indicates the presence of the processed forms (estimated at 1–15%) in the formulated bulk drug substance; "–" indicates the absence of the processed forms.

Figure 4A:
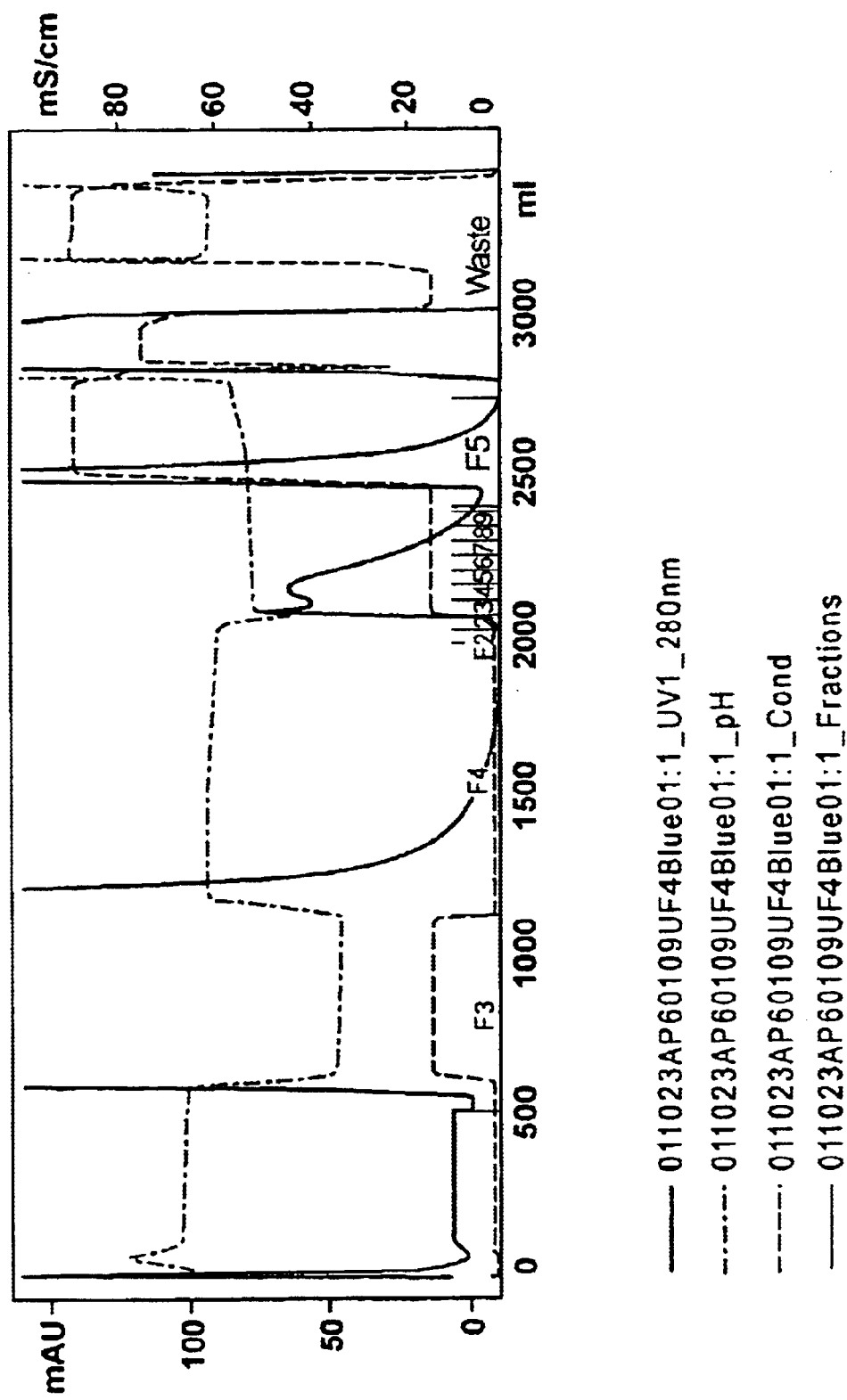
FIGS. 4A–4C depicts results obtained for the chromatograms of the Blue Sepharose Column (FIG. 4A), Copper Chelating Sepharose Column (FIG. 4B) and Phenyl Sepharose Column (FIG. 4C).
Figure 4B:
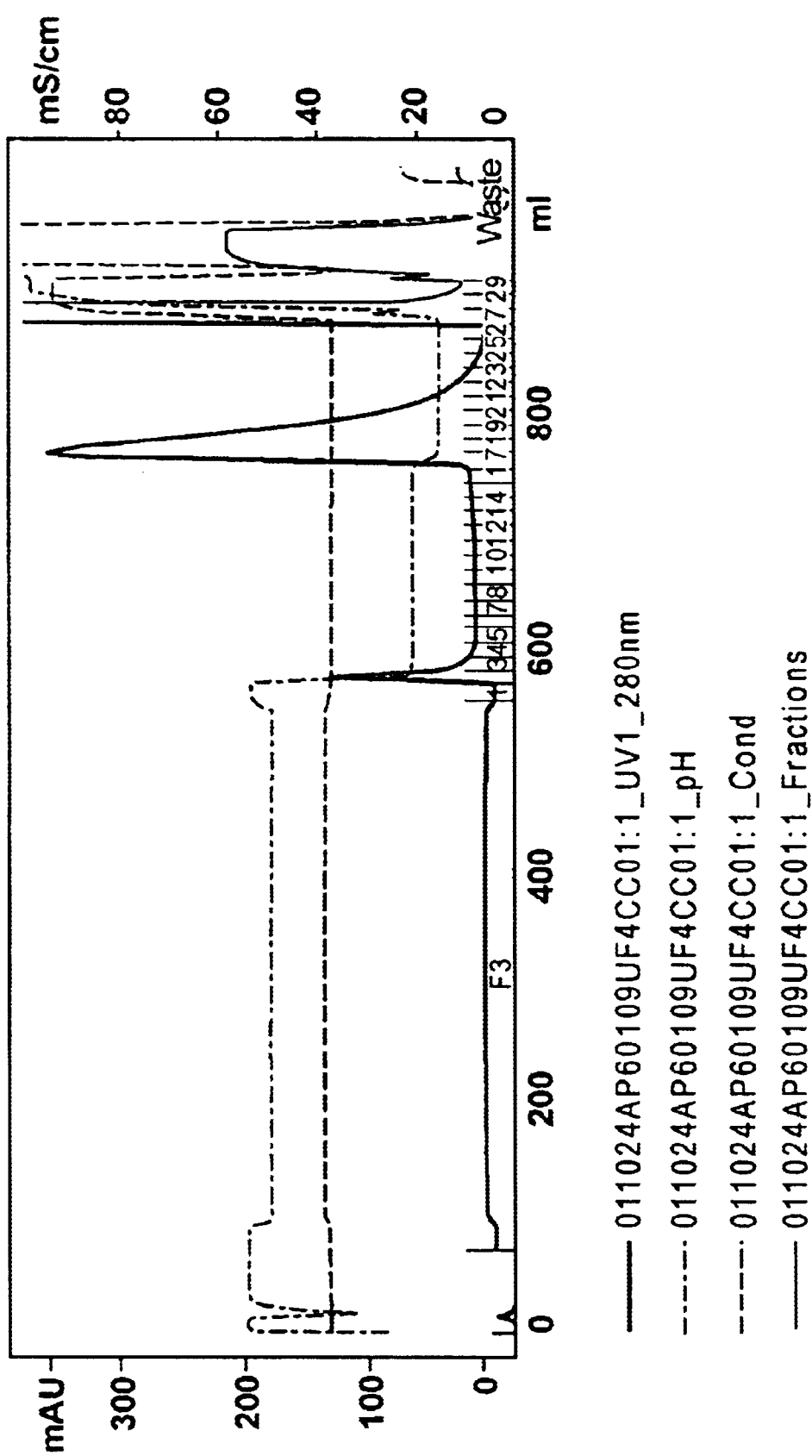
Figure 4C:
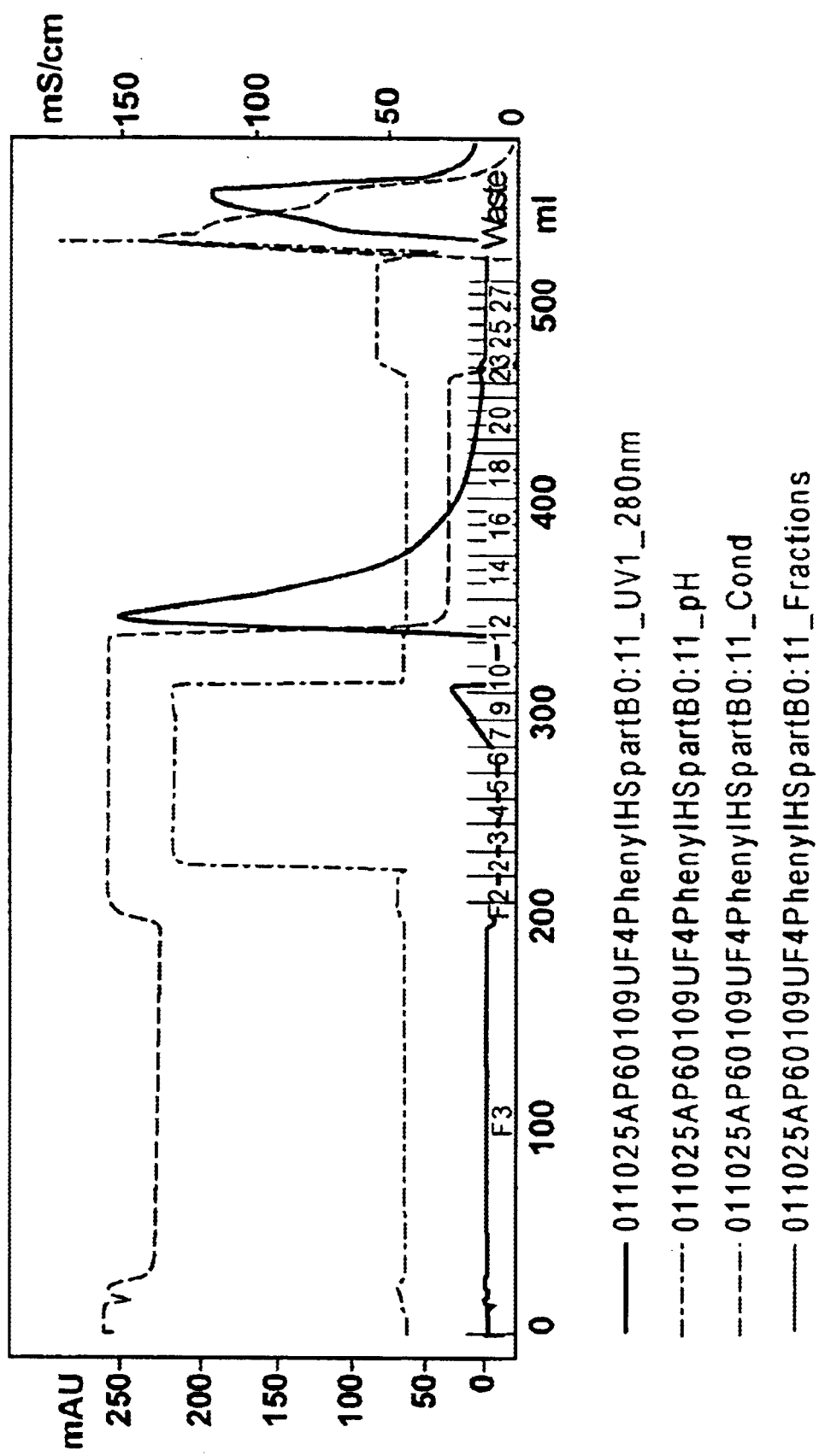
Figure 5:
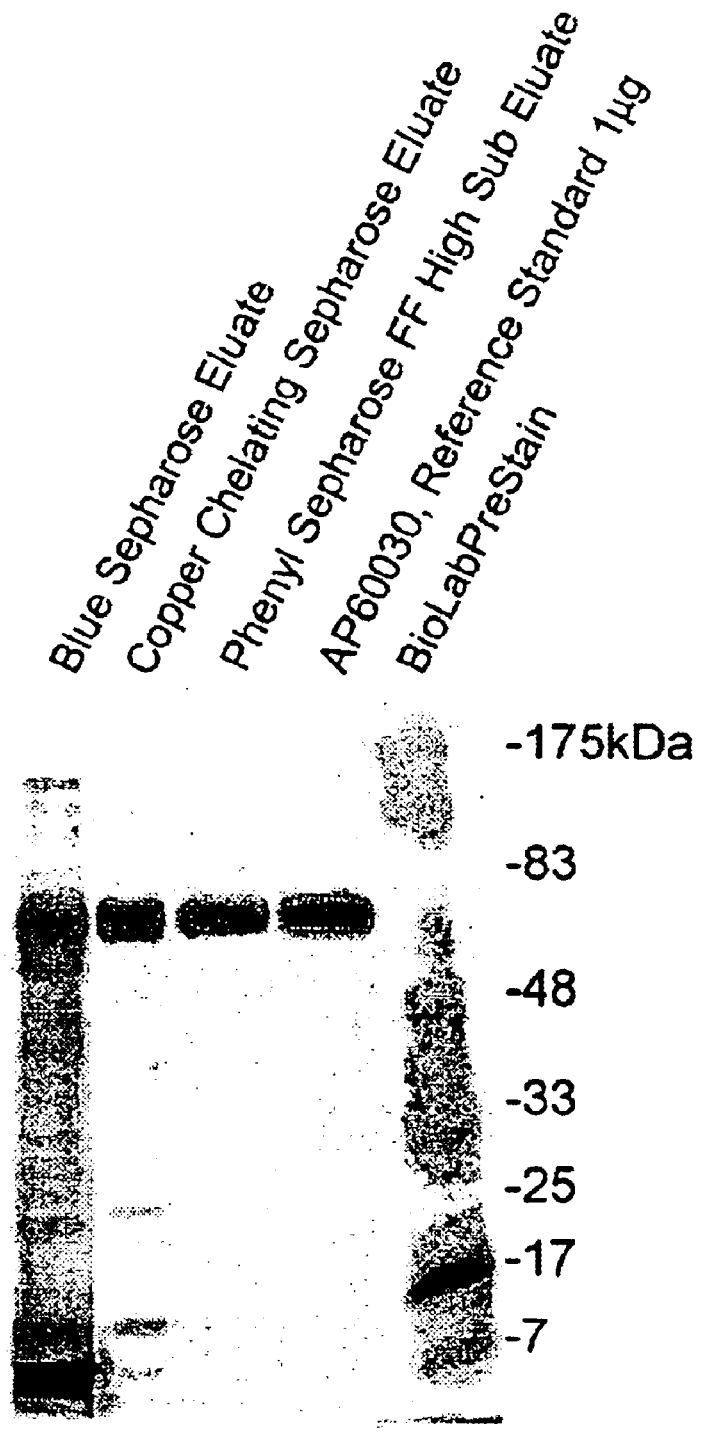
FIG. 5 depicts a 4–20% polyacrylamide gradient gel showing the result of a silver-stained SDS-PAGE of the perfusion process purification method (Tables 14 and 15).
Figure 6A:
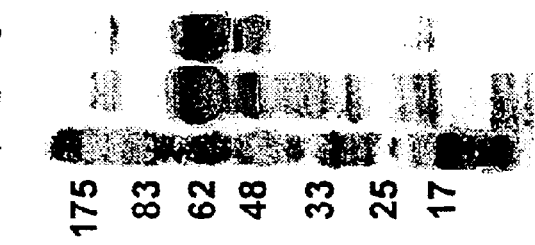
Figure 6B:
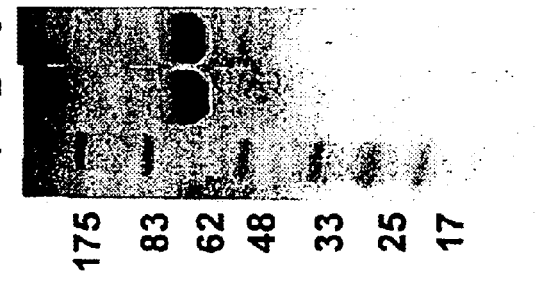
Figure 6C:
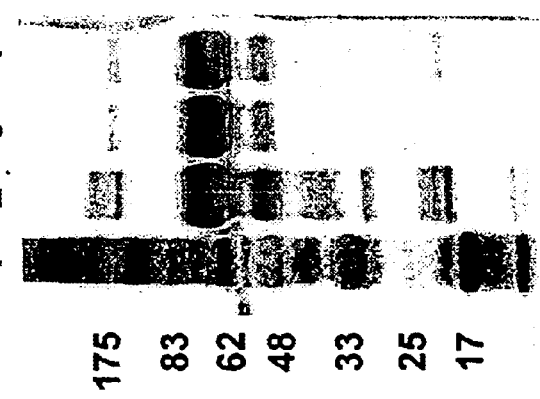
Figure 6D:
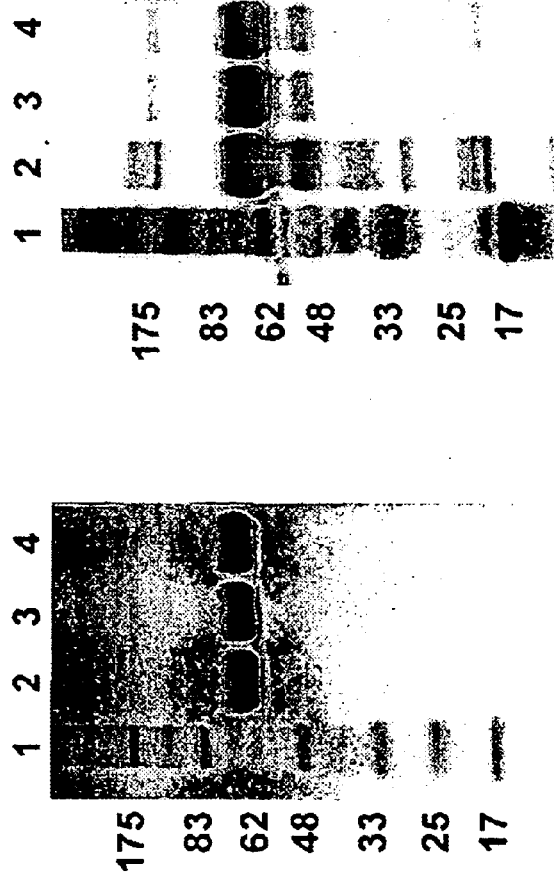
Figure 7A:
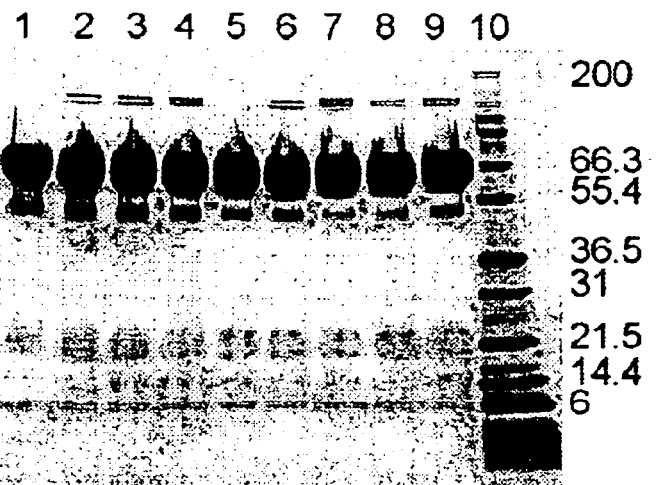
FIG. 7A depicts the results on silver-stained 4–20% polyacrylamide gradient SDS gels.
Figure 7B:
FIG. 7B depicts the results on Coomassie stained 4–20% polyacrylamide gradient SDS gels. Lane 1, lot AP60202 UF4; lane 2, lot AP60202 UF10; lane 3, lot AP60202 UF18; lane 4, lot AP60202 (BMK); lane 5, lot 102PD0139x B3; lane 6, lot 102PD0139x B5; lane 7, perfusion reference standard rhASB-202–002; lane 8, lot 102PD0139 P1; lane 9, lot 102PD0139 P2; and, lane 10, Mark 12 standard (MW in kDa).

FIGS. 4A–4C provide the representative chromatograms of the three chromatographic steps of the perfusion method of purification (Table 16). Table 22 provides the average recoveries of precursor rhASB for each of these three chromatographic steps. FIG. 5 provides the data for the purity analysis of in-process samples at each chromatographic step and of the purified final product (precursor rhASB).

TABLE 22

Summary of Purification Recoveries.

| Step | Average Recovery (%) |
|---|---|
| pH Adjustment to 5.0 | 83 |
| Blue Sepharose Column | 84 |
| Copper Chelating Sepharose Column | 86 |
| Copper to Phenyl Transition | 86 |
| Phenyl Sepharose Column | 88 |
| Overall | 50 |

When purified products obtained using the batch process and the perfusion process are compared, the perfusion process clearly produces a purer precursor rhASB. The perfusion process is able to produce consistent precursor rhASB purity of 99% or more, while the batch process does not (Table 21). FIG. 6 provides a comparison between the products obtained using the old batch method wherein the cell culture is cultured using a medium that is supplemented with G418 and not supplemented with folic acid, serine and asparagine (lane 2), and the purified products purified using the perfusion process (lanes 3–9)). The samples of rhASB were denatured in SDS with a reducing agent and subjected to electrophoresis through 4–20% PAGE in SDS running buffer. The batch process purified products clearly contain far more impurities (especially near the 48 kDa size) than the perfusion process purified products. The batch process rhASB appear to have a purity of less than 95% (lane 2). The perfusion process purified lots are highly comparable to each other and are significantly less complex than the batch process purified rhASB standard, indicating a higher degree of purity for the perfusion process material.

Table 23 provides percent purity of precursor rhASB purified using the perfusion process purification method.

TABLE 23

Purity of Final Product.

| Lot | Purity by RP-HPLC (% main peak) |
|---|---|
| AC60109 UF #4 | 99.8 |
| AC60109 UF #10 | 99.6 |
| AC60109 UF #1 | 99.7 |
| AC60109 UF #18 | 99.9 |
| AC60109A UF #22 | 99.7 |
| AC60109A UF #25 | 99.8 |
| AC60109A UF #27 | 100 |
| AC60109 | 99.8 |
| BMK Manufacturing | |
| AC60202 UF #4 | ND |
| AC60202 UF #10 | ND |
| AC60202 UF #18 | ND |
| AC60202 | 100 |
| BMK Manufacturing | |
| Average | 99.8 |

ND = not determined.

Protease Removal in the Perfusion Process

At the 180 L batch scale two relatively large 24 L DEAE Sepharose runs are required per lot. The perfusion process generates 10-fold larger harvest volumes that impose severe impractical DEAE Sepharose column sizes and buffer volumes for practicval large scale purification. Therefore, elimination of the particularly untenable DEAE Sepharose step was evaluated in an effort to streamline the new perfusion purification train. As a consequence, the three column train (as described in Table 16) overcomes this large scale production obstacle.

The DEAE Sepharose chromatography step in the batch process (described in Table 15) was employed primarily to remove total protein (including proteases) and the pH indicator dye, Phenol Red. The latter issue is addressed in the new process by removal of Phenol Red from the 302 media formulation. The removal of total protein by DEAE sepharose step resulted in higher Blue sepharose capacity at pH 5.5. In the new process, Blue Sepharose conditions needed to be identified that balanced high rhASB capacity while limiting protease activity. Both capacity and proteolysis are enhanced at low pH. In addition, clearance of proteases should be demonstrable to improve the robustness of the subsequent Copper Chromatography step, where clearance of the protease, cathepsin, has been found problematic in the Batch process. Conditions were found which yielded the desired results, whereby, loading was performed at low pH, while wash and elution conditions were at higher pH, conditions that efficiently clear the protease, cathepsin, with an acceptable load of 0.8 mg rhASB/ml resin. Removal of the protease activity (e.g. cathepsin) is demonstrated in the chromatograms of FIG. 8.

Figure 9B:
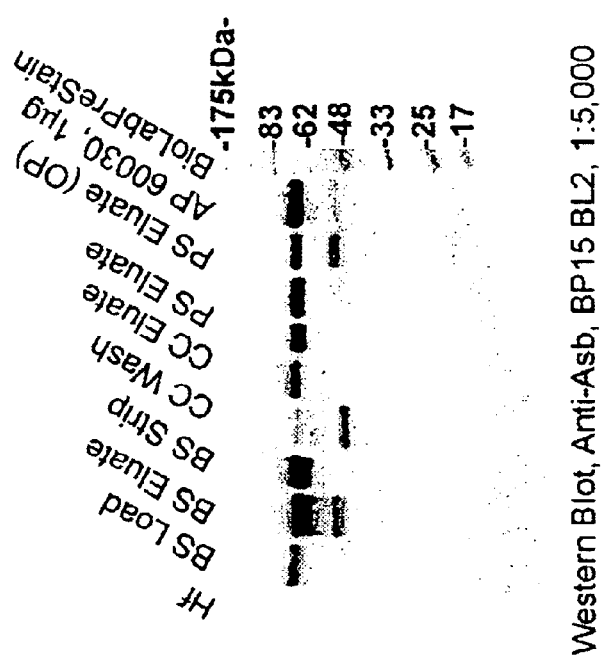
FIG. 9B depicts the results of the proteins transferred from the gel of FIG. 9A transferred onto nitrocellulose and probed by anti-rhASB antibodies.
Figure 9A:
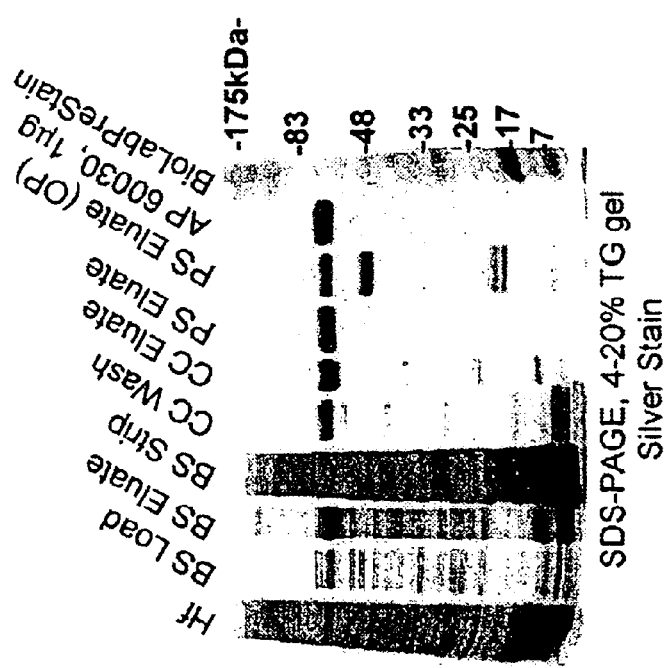
FIG. 9A depicts the results of a silver-stained 4–20% polyacrylamide gradient SDS gels.
Figure 9C:
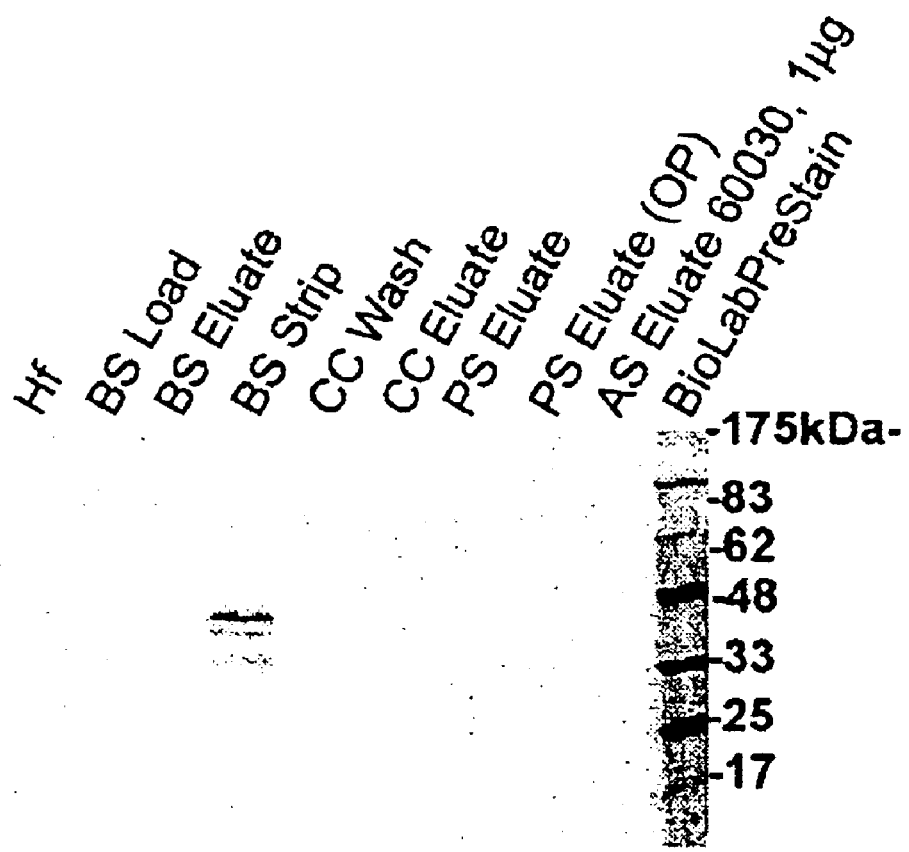
FIG. 9C depicts the results of the proteins transferred from the gel of FIG. 9A transferred onto nitrocellulose and probed by anti-cathepsin antibodies. BioLab-PreStain indicates molecular weight standards (MW in kDa).

Comparison of rhASB purified from perfusion run, 102PD0055, using either the new process (without DEAE FT chromatography) or old Batch purification process (PS Eluate (OP) indicate that the old process material purified (using the batch method) from the same reactor run, lane PS Eluate (OP), has significant more proteolysis, as demonstrated by the additional bands on silver-stained gel and detectible by anti-ASB antibodies (see FIG. 9). The new process is much purer relative to the batch standard. The cathepsin protease is cleared by Blue chromatography. Anti-cathepsin cross-reactive material is seen in the Blue Strip fraction using the new process.

Although the invention has been described with reference to the presently preferred embodiments, it should be understood that various modifications can be made without departing-from the spirit of the invention. Accordingly, the invention is limited only by the following claims.

What is claimed is:

1. A composition comprising precursor human N-acetylgalactosamine-4-sulfatase, wherein said precursor N-acetylgalactosamine-4-sulfatase has a purity of at least equal to or greater than 99% based on total protein wherein said purity is measured using the reverse-phase HPLC method, and wherein the composition is free of detectable bands of about 47–48 kDa upon sodium dodecyl sulfate polyacrylamide gel electrophoresis (SDS-PAGE) with Coomassie stain.

2. The composition according to claim 1, wherein said precursor N-acetylgalactosamine-4-sulfatase has a purity of at least equal to or greater than 99.2% based on total protein wherein said purity is measured using the reverse-phase HPLC method.

3. The composition according to claim 1, wherein said precursor N-acetylgalactosamine-4-sulfatase is glycosylated.

4. The composition according to claim 1, wherein said purity is equal to or greater than 99.5%.

5. The composition according to claim 4, wherein said purity is equal to or more than 99.9%.

6. The composition according to claim 1, wherein said precursor N-acetylgalactosamine-4-sulfatase is a recombinant precursor N-acetylgalactosamine-4-sulfatase.

7. The composition according to claim 6, wherein said recombinant precursor N-acetylgalactosamine-4-sulfatase is a recombinant human precursor N-acetylgalactosamine-4-sulfatase.

8. The composition according to claim 7 wherein said recombinant human precursor N-acetylgalactosamine-4-sulfatase is secreted from mammalian cells in culture transfected with a DNA sequence encoding human N-acetylgalactosamine-4-sulfatase.

9. The composition according to claim 7 wherein said mammalian cells are Chinese Hamster Ovary cells.

10. A pharmaceutical composition comprising the composition according to claim 1 and a pharmaceutically acceptable carrier.

11. The pharmaceutical composition of claim 10 further comprising a sodium chloride solution and a non-ionic detergent.

12. The pharmaceutical composition of claim 10 wherein the precursor N-acetylgalactosamine-4-sulfatase is present at a concentration of about 1–5 mg/mL or about 50 to about 250 Units per mL.

13. The pharmaceutical composition of claim 10 wherein the buffer is a sodium phosphate buffer at a concentration of about 10–50 mM.

14. The pharmaceutical composition of claim 10 wherein the pH of the solution is maintained at about 5.8.

15. The pharmaceutical composition of claim 10 further comprising polyoxyethylenesorbitan 20 or 80.

16. The pharmaceutical composition of claim 15, wherein the concentration of said polyoxyethylenesorbitan 20 or 80 is about 0.005% by volume.

17. A method for treating a subject suffering from a deficiency in N-acetylgalactosamine-4-sulfatase comprising the step of administering to a subject in need of such treatment an effective amount of the composition according to claim 1, 2, 4, or 5.

18. The method of claim 17 wherein the subject is suffering from a mucopolysaccharidosis.

19. The method of claim 18 wherein the mucopolysaccharidosis is MPS VI.

20. The method of claim 17 wherein the mucopolysaccharidosis is Maroteaux-Lamy Syndrome.

21. The method of claim 17 wherein said subject has about 50% or less of a normal N-acetylgalactosamine-4-sulfatase activity.

22. The method of claim 17 wherein at least about 50 Units/kg or at least about 1 mg/kg of said precursor N-acetylgalactosamine-4-sulfatase is administered weekly to said subject.

23. The method of claim 17 wherein at least about 100 units or 2.0 mg/kg of said precursor N-acetylgalactosamine-4-sulfatase is administered weekly to said subject.

24. A method to purify a precursor human N-acetylgalactosamine-4-sulfatase of claim 1 comprising:
(a) obtaining a fluid containing precursor N-acetylgalactosamine-4-sulfatase;
(b) reducing the proteolytic activity of a protease in said fluid able to cleave the precursor N-acetylgalactosamine-4-sulfatase, wherein said reducing does not harm said precursor N-acetylgalactosamine-4-sulfatase;
(c) contacting the fluid with a Cibracon blue dye interaction chromatography resin;
(d) contacting the fluid with a copper chelation chromatography resin;
(e) contacting the fluid with a phenyl hydrophobic interaction chromatography resin;
(f) recovering said precursor N-acetylgalactosamine-4-sulfatase at a purity of at least equal to or greater than 99% based on total protein wherein said purity is measured using the reverse-phase RPLC method, and wherein the composition is free of detectable bands of about 47–48 kDa upon sodium dodecyl sulfate polyacrylamide gel electrophoresis (SDS-PAGE) with Coomassie stain.

25. The method of claim 24 wherein said obtaining comprises growing a culture of cells transformed with a gene encoding N-acetylgalactosamine-4-sulfatase.

26. The method of claim 25 wherein said gene encoding human N-acetylgalactosamine-4-sulfatase encodes a protein 533 amino acids in length.

27. The method of claim 25 wherein said cells are mammalian cells.

28. The method of claim 27 wherein said mammalian cells are Chinese Hamster Ovary cells.

29. The method of claim 25 wherein said obtaining further comprises harvesting the fluid from said culture of cells.

30. The method of claim 24 wherein said obtaining further comprises concentrating said fluid to about 20×.

31. The method of claim 24 wherein said reducing comprises adjusting the pH of the fluid to equal to or less than 8.0.

32. The method of claim 31 wherein said reducing comprises adjusting the pH of the fluid to about 4.8 to 5.5.

33. The method of claim 32 wherein said reducing comprises adjusting the pH of the fluid to about 4.8 to 5.2.

34. The method of claim 24 wherein step (c) comprises passing the fluid through a Cibracon blue dye interaction chromatography column.

35. The method of claim 34 wherein said Cibracon blue dye interaction chromatography column is a Blue Sepharose 6 Fast Flow column.

36. The method of claim 24 wherein step (d) comprises passing the fluid through a copper chelation chromatography column.

37. The method of claim 36 wherein said copper chelation chromatography column is a Chelating Sepharose Fast Flow column.

38. The method of claim 24 wherein step (e) comprises passing the fluid through a phenyl hydrophobic interaction chromatography column.

39. The method of claim 38 wherein said phenyl hydrophobic interaction chromatography column is a Phenyl Sepharose 6 Fast Flow High Sub column.

40. The method of claim 24 wherein the temporal sequence of steps (c), (d) and (e) is step (c), step (d) and step (e).

41. The method of claim 24 wherein said recovering comprises diafiltration of the fluid.

42. The method of claim 24 wherein said recovering comprises filtering the fluid to remove DNA.

43. The method of claim 26 wherein said recovering comprises filtering the fluid to remove virus.

44. The method of claim 43 wherein said filtering comprises passing said fluid through a 0.2 μm filter.

45. The method of claim 24 wherein said purity is measured using the reverse-phase HPLC method.

46. The method of claim 24 wherein said fluid does not contact a DEAE Sepharose resin.

47. A composition comprising precursor human N-acetylgalactosamine-4-sulfatase with a purity of at least equal to or greater than 99% wherein the composition is free of detachable bands of about 47–48 kDa upon SDS-PAGE with Coomassie stain, obtained by the method comprising (a) obtaining a fluid containing precursor human N-acetylgalactosamine-4-sulfatase;

(b) reducing the proteolytic activity of a protease in said fluid able to cleave the precursor N-acetylgalactosamine-4-sulfatase, wherein said reducing does not harm said precursor N-acetylgalactosamine-4-sulfatase;

(c) contacting the fluid with a Cibracon blue dye interaction chromatography resin;

(d) contacting the fluid with a copper chelation chromatography resin;

(e) contacting the fluid with a phenyl hydrophobic interaction chromatography resin;

(f) recovering said precursor human N-acetylgalactosamine-4-sulfatase.

* * * * *

UNITED STATES PATENT AND TRADEMARK OFFICE
CERTIFICATE OF CORRECTION

PATENT NO. : 6,866,844 B2
DATED : March 15, 2005
INVENTOR(S) : Qin et al.

It is certified that error appears in the above-identified patent and that said Letters Patent is hereby corrected as shown below:

Column 54,
Line 39, delete "RPLC" and insert -- HPLC --.

Column 56,
Line 5, delete "99%" and insert -- 99%, --.
Line 7, delete "by the method" and insert -- by a method --.

Signed and Sealed this

Twenty-seventh Day of September, 2005

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 6,866,844 B2 |
| APPLICATION NO. | : 10/290908 |
| DATED | : March 15, 2005 |
| INVENTOR(S) | : Qin et al. |

Page 1 of 1

It is certified that error appears in the above-identified patent and that said Letters Patent is hereby corrected as shown below:

At item (63) on the cover page, "Continuation-in-part of application No. 10/704,365, filed on November 7, 2003." should be deleted.

At col. 1, lines 7-8, "This application is a Continuation-in-part of U.S. Ser. No. 10/704,365, filed Nov. 7, 2003, now pending." should be deleted.

At col. 56, line 6, in claim 47, "detachable" should be --detectable--.

Signed and Sealed this

Twenty-fourth Day of April, 2007

JON W. DUDAS
*Director of the United States Patent and Trademark Office*